US012414830B2

(12) United States Patent
Zhang et al.

(10) Patent No.: US 12,414,830 B2
(45) Date of Patent: Sep. 16, 2025

(54) INTEGRATED ROBOTIC SYSTEM FOR RAPID ENDOLUMINAL DELIVERY OF MINIATURE ROBOTS

(71) Applicant: Multi-Scale Medical Robotics Center Limited, Hong Kong (CN)

(72) Inventors: Li Zhang, Hong Kong (CN); Wai Yan Philip Chiu, Hong Kong (CN); Kai Fung Chan, Hong Kong (CN); Ben Wang, Hong Kong (CN)

(73) Assignee: Multi-Scale Medical Robotics Center Limited, Hong Kong (CN)

( * ) Notice: Subject to any disclaimer, the term of this patent is extended or adjusted under 35 U.S.C. 154(b) by 1127 days.

(21) Appl. No.: 17/350,777

(22) Filed: Jun. 17, 2021

(65) Prior Publication Data

US 2021/0393356 A1    Dec. 23, 2021

Related U.S. Application Data

(60) Provisional application No. 63/040,049, filed on Jun. 17, 2020.

(51) Int. Cl.
*A61B 34/00* (2016.01)
*A61B 34/20* (2016.01)
(Continued)

(52) U.S. Cl.
CPC .............. *A61B 34/72* (2016.02); *A61B 34/20* (2016.02); *A61B 90/36* (2016.02);
(Continued)

(58) Field of Classification Search
CPC ...... A61B 2034/2051; A61B 2034/301; A61B 2090/374; A61B 2090/376;
(Continued)

(56) References Cited

U.S. PATENT DOCUMENTS

2017/0020623 A1*  1/2017  Glossop ................. A61B 90/11
2019/0359928 A1*  11/2019  Choi ....................... C12M 23/16
(Continued)

OTHER PUBLICATIONS

Chan, K. F., & Zhang, L. (2019). Magnetic stem cell spheroid microrobots and their in vivo applications (thesis). Magnetic stem cell spheroid microrobots and their in vivo applications. ProQuest LLC, Ann Arbor. (Year: 2019).*

(Continued)

*Primary Examiner* — Charles A Marmor, II
*Assistant Examiner* — Marc D. Honrath
(74) *Attorney, Agent, or Firm* — SALIWANCHIK, LLOYD & EISENSCHENK

(57) ABSTRACT

An integrated robotic system and methods for delivery and on-demand tasks of magnetic devices in a body for different clinical applications are provided. The integrated robotic system includes a magnetic actuation device, a plurality of imaging devices, a delivery device, and at least one magnetic device. The magnetic actuation device includes a permanent magnet or an electromagnetic coil system, and a controller for controlling the magnetic device. The plurality of imaging devices include two or more imaging modalities for capturing images of the magnetic device and tracking locations of the magnetic device in the body. The magnetic device includes one or more selected from a millimeter-sized robot, a microrobot, a nanorobot, a microrobotic swarm, and particles or drugs that respond to a magnetic field and small enough to be delivered by the delivery device.

13 Claims, 20 Drawing Sheets

(51) Int. Cl.
*A61B 34/30* (2016.01)
*A61B 90/00* (2016.01)

(52) U.S. Cl.
CPC . *A61B 2034/2051* (2016.02); *A61B 2034/301* (2016.02); *A61B 2090/374* (2016.02); *A61B 2090/3762* (2016.02); *A61B 2090/3778* (2016.02); *A61B 2562/0223* (2013.01)

(58) Field of Classification Search
CPC ...... A61B 2090/3762; A61B 2090/378; A61B 2090/3782; A61B 2562/0223; A61B 34/20; A61B 34/72; A61B 34/73; A61B 90/36; A61B 90/37
See application file for complete search history.

(56) References Cited

U.S. PATENT DOCUMENTS

| | | | | |
|---|---|---|---|---|
| 2020/0100658 | A1* | 4/2020 | Abbott | A61B 1/0051 |
| 2020/0360711 | A1* | 11/2020 | Kidd | A61N 2/002 |
| 2021/0052190 | A1* | 2/2021 | Kiselyov | G01R 33/287 |

OTHER PUBLICATIONS

Field, R. D., Anandakumaran, P. N., & Sia, S. K. (2019). Soft medical microrobots: Design Components and System Integration. Applied Physics Reviews, 6(4), 041305. https://doi.org/10.1063/1.5124007 (Year: 2019).*

Li, J., et al., "Micro/nanorobots for biomedicine: Delivery, surgery, sensing, and detoxification," Science Robotics, 2017, 2:1-9.

Li, W., et al., "Microfluidic fabrication of microparticles for biomedical applications," Chemical Society Reviews, 2018, 47(15):1-39.

Wu, Z., et al., "A microrobtic system guided by photoacoustic computed tomography for targeted navigation in intestines in vivo," Science Robotics, 2019, 4:1-11.

Esteban-Fernandez De Avila, B., et al., "Hybrid biomembrane-functionalized nanorobots for concurrent removal of pathogenic bacteria and toxins," Science Robotics, 2018, 3:1-9.

Li, J., et al., "Development of a magnetic microrobot for carrying and delivering targeted cells," Science Robotics, 2018, 3:1-11.

Jeon, S., et al., "Magnetically actuated microrobots as a platform for stem cell transplantation," Science Robotics, 2019, 4:1-11.

Medina-Sanchez, M., et al., "Cellular Cargo Delivery: Toward Assisted Fertilization by Sperm-Carrying Micromotors," Nano Letters, 2016, 16:555-561.

Yan, X., et al., "Multifunctional biohybrid magnetite microrobots for imaging-guided therapy," Science Robotics, 2017, 2:1-14.

Yan, X., et al., "Magnetite Nanostructured Porous Hollow Helical Microswimmers for Targeted Delivery," Advanced Functional Materials, 2015, 25:5333-5342.

Felfoul, O., et al., "Magneto-aerotactic bacteria deliver drug-containing nanoliposomes to tumour hypoxic regions," Nature Nanotechnology, 2016, 11:1-9.

Martel, S., et al., "MRI-based Medical Nanorobotic Platform for the Control of Magnetic Nanoparticles and Flagellated Bacteria for Target Interventions in Human Capillaries," The International Journal of Robotics Research, 2009, 28(9):1169-1182.

Zhang, Y., et al., "Enhanced Removal of Toxic Heavy Metals Using Swarming Biohybrid Adsorbents," Advanced Functional Materials, 2018, 28(1806340):1-9.

Wang, X., et al., "3D Printed Enzymatically Biodegradable Soft Helical Microswimmers," Advanced Functional Materials, 2018, 28(1804107):1-8.

Laschi, C., et al., "Soft robotics: Technologies and systems pushing the boundaries of robot abilities," Science Robotics, 2016, 1:1-11.

Medina-Sanchez, M., et al., "Swimming Microrobots: Soft, Reconfigurable, and Smart," Advanced Functional Materials, 2018, 28(1707228):1-27.

Huang, H.-W., et al., "Soft micromachines with programmable motility and morphology," Nature Communications, 2016, 7(12263):1-10.

Morimoto, Y., et al., "Biohybrid robot powered by an antagonistic pair of skeletal muscle tissues," Science Robotics, 2018, 3:1-10.

Zhao, X., et al., "Soft microbots controlled by nanomagnets," Nature, 2019, 575:58-59.

Ahmed, D., et al., "Neutrophil-inspired propulsion in a combined acoustic and magnetic field," Nature Communications, 2017, 8(770):1-8.

* cited by examiner

| Sample | Elastic modulus (kPa) |
|---|---|
| Polyethylene (PE) | $3.5 \times 10^4$ |
| Rubber | $7.84 \times 10^3$ |
| Articular cartilage | $2.75 \times 10^4$ |
| Nasal cartilage | $\sim 5 \times 10^3$ |
| Face skin | 5.6~11 |
| Red blood cell | 0.1~0.2 |
| MSCSM | 2.2 |

B     Actuation and Imaging

| Location of MSCSMs | Imaging mode | Actuation mode |
|---|---|---|
| *Stage 0:* Outside→stomach→intestine | Endoscopy | Endoscopic access |
| *Stage 1:* In intestine | Endoscopy | Magnetic field |
| *Stage 2:* Intestine→bile duct | Endoscopy | Magnetic field |
| *Stage 3:* In bile duct | US imaging | Magnetic field |

| | Process | Distance | Time |
|---|---|---|---|
| Stage 0 | Endoscope entering duodenum | 90 cm | 30 s |
| | Microrobots passing through the catheter | 90 cm | 5s |
| Stage 1 | Actuation of MSCSMs in intestine | <5 cm | ~1 min |
| Stage 2 | Magnetic attraction of MSCSMs into bile duct | < 1cm | ~1 min |
| Stage 3 | Actuation of MSCSMs in bile duct | ~5cm | ~1 min |

INTEGRATED ROBOTIC SYSTEM FOR RAPID ENDOLUMINAL DELIVERY OF MINIATURE ROBOTS

CROSS-REFERENCE TO RELATED APPLICATION

This application claims the benefit of U.S. Provisional Application Ser. No. 63/040,049, filed Jun. 17, 2020, which is hereby incorporated by reference in its entirety including any tables, figures, or drawings.

BACKGROUND OF THE INVENTION

Microrobots have received intensive development in recent years for directed actuation and localized delivery inside a human body for various biomedical applications including drug delivery, sensing and diagnosis, minimally invasive surgery, and thrombus ablation. Magnetic field actuated microrobots, in particular, offer an optimal option towards in vivo applications due to their deep penetration and safe feature compared with other types of actuation modes.

Despite the substantial progresses that microrobots have made, suitable delivery method, tracking and control techniques are still lacking for the development of clinical applications of the microrobots. Although the targeted delivery of the microrobots into organ-scale tissues and large cavities, such as the gastrointestinal (GI) tract, has been realized, it is rather difficult to access certain human body regions such as small cavities and tortuous ducts by the microrobots with vision-based control, making the delivery to these hard-to-reach regions highly challenging.

Further, although the magnetic actuation unit can perform high-precision navigation of microrobots, the high motion precision inevitably results in travels over a long distance, making the whole-body scale navigation of the robots time-consuming and less efficient. There is no report yet for precisely localized delivery of microrobots with a long distance across the complex and dynamic in vivo environment to the deep and narrow space. Endoscopy, as a surgical tool, may enter the human body via natural orifices and is known for its capability to perform long-distance and rapid deployment in a variety of organs with real-time feedback under the endoscopic view. However, endoscopy has only limited accessibility to deep interior regions within tortuous ducts.

Therefore, there are still a variety of regions inside the human body that can be hardly accessed by clinical endoscope and medical robots. Certain parts of the inaccessible regions are even invisible by endoscopes, making the delivery towards these hard-to-reach and hard-to-see regions highly challenging.

BRIEF SUMMARY OF THE INVENTION

There continues to be a need in the art for improved designs and techniques for directed actuation and localized delivery of microrobots to hard-to-reach and hard-to-see regions inside a human or animal body.

Embodiments of the subject invention pertain to an integrated robotic system and methods for delivery and on-demand tasks of magnetic devices in a body for different clinical applications.

According to an embodiment of the subject invention, the integrated robotic system can comprise a magnetic actuation device, a plurality of imaging devices, a delivery device, and at least one magnetic device, wherein the delivery device is configured to deliver the at least one magnetic device to a targeted location of the body. The magnetic actuation device comprises a permanent magnet or an electromagnetic coil system, and a controller, for controlling the magnetic device. The plurality of imaging devices comprises two or more selected from an endoscopy, a ultrasound imaging, a fluoroscopy, a magnetic resonance imaging, a positron emission tomography, a X-ray computed tomography, a photoacoustic imaging, a fluorescence imaging, a digital camera and magnetic field sensors for capturing images of the magnetic device and tracking locations of the magnetic device in the body. The delivery device is an endoscope, a catheter, a guidewire, or a tube. The magnetic device comprises one or more selected from a millimeter-sized robot, a microrobot, a nanorobot, a microrobotic swarm, and particles or drugs that respond to a magnetic field and small enough to be delivered by the delivery device. Moreover, the body can be a part of an animal or a human, including one or more selected from a gastrointestinal tract, a brain, an ear, a nose, a throat, an eye, a blood vessel, a heart, a respiratory tract, a liver, a pancreas, a hepatopancreatic duct, a urinary tract, and a reproductive tract. The clinical applications are diagnostic and/or therapeutic applications comprising one or more selected from a targeted delivery of microrobots, drugs or cells; retrieval of microrobots, drugs, or cells; sensing; tissue manipulation; tissue removal; and tissue retraction. Further, the magnetic device can be a soft magnetic microrobot configured to react to surroundings by self-alternating a shape or structure of the soft magnetic microrobot. The soft magnetic microrobot is formed by cells and magnetic particles aggregated intercellularly without a rigid scaffold. When being compressed, the soft magnetic microrobot recovers to original shapes and structures after the compression is retracted. After the magnetic device is delivered to at the targeted location, the magnetic device is fixed to the targeted location against a fluid flow of up to about 108 mm/s. The amount of magnetic particle doping the stem cell spheroid is smaller than 2%. When the soft magnetic microrobot passes through a narrow channel with an inner width smaller than the diameter of the soft microrobots, the soft magnetic microrobot recovers the shape or the structure after the reconfigurable passing process.

In certain embodiment, a method for controlling an integrated robotic system that comprises a magnetic actuation device, a plurality of imaging devices, a delivery device, and at least one magnetic device for delivering the at least one magnetic device to a targeted location of a body is provided. The method comprises controlling delivery motions of at least one magnetic device to perform a long-range delivery step and a precise magnetic actuation delivery step. During the long-range delivery step, the delivery device is controlled to move the magnetic device to travel a long distance to a region in proximity of the targeted location in the body. During the precise magnetic actuation delivery step, the magnetic actuation device is controlled to move the magnetic device with high precision to the targeted location in the body after the long-range delivery step. Moreover, during the long-range delivery step, a first imaging device of the imaging devices is configured to capture images of the magnetic device and track locations of the magnetic device in the body. During the precise magnetic actuation delivery step, a second device of the imaging devices is configured to capture images of the magnetic device and track locations of the magnetic device in the body.

BRIEF DESCRIPTION OF THE DRAWINGS

The objects, features and advantages of the present invention will be more clearly described from the following drawings and description but are by no means limited to the following drawings and description.

FIGS. 1B-1E showing an example of the active delivery process to the difficult-to-access and narrow bile duct wherein FIG. 1B showing manipulation of the endoscope from outside to the stomach, and finally arriving at the intestine, the inset showing a photograph of the catheter-based delivery of soft microrobots at a delivery speed of approximately 30 cm/s with controlled numbers (scale bar is 1 mm), wherein FIG. 1C showing rapid deployment of the soft microrobots to the intestine through the catheter equipped inside the endoscope, wherein FIG. 1D showing magnetic actuation of the soft microrobots from the intestine to the entrance of the bile duct under the real-time endoscopic view at a delivery speed of approximately 2 mm/s, wherein when the soft microrobots arrive at the entrance site, a strong magnetic field is applied to pull the microrobots into the bile duct in a self-adaptable and resilient fashion, and wherein FIG. 1E showing that in the bile duct, the soft microrobots are actuated under real-time US imaging of multiple organs; according to an embodiment of the subject invention.

FIG. 2B showing scanning electron microscopy (SEM) images of integral and enlarged views of an MSCSM; FIG. 2C showing SEM image of the inner distribution of the stem cells (pink) and the magnetic particles (blue); FIG. 2D showing Bright-field (BF) images of the as-prepared MSCSMs with various initial cell numbers including 20 k cells, 50 k cells, 100 k cells, and 200 k cells (scale bar is 500 µm); FIG. 2E showing confocal laser scanning microscopy (CLSM) images of the morphologies of MSCSMs containing different amounts of magnetic particles; FIG. 2F having a bar graph showing the size of MSCSMs with different initial cell numbers and different amounts of magnetic particles; FIG. 2G showing cell viability of MSCSMs with different concentrations of magnetic particles, wherein the initial cell numbers are 20 k, 50 k and 100 k, respectively and cell viability of MSCSMs with 10 µg magnetic particles and different initial cell numbers; according to an embodiment of the subject invention.

FIG. 3B showing the compression and shearing of the MSCSMs using rheometer (diameter of 500 µm, stage gap of 100 µm); FIG. 3C showing snapshots of the compression process of an MSCSM wherein the shape of the MSCSM recovered after the retraction of the compression; FIG. 3D showing storage modulus G' and loss modulus G" as functions of frequency; FIG. 3E showing a table of typical elastic moduli of some materials and common biological samples; and FIG. 3F showing snapshots of the deformation of the MSCSM when it passes through narrow gaps with different widths, indicating the elasticity of the MSCSMs, according to an embodiment of the subject invention.

FIG. 4N showing a bar graph of the open wound area of the MSCSMs group and the control group (measured using the image of FIG. 4J), wherein the percentage change is calculated by the formula (open wound area at 15 h)/(open wound area at 0 h)×100. * $P<0.05$ and compared to the control group, and scale bars in FIGS. 4G, 4J, 4L, and 4M are 500 µm, according to an embodiment of the subject invention.

FIG. 5C showing successive optical images of the actuation of a swarm of MSCSMs in the pig's stomach toward the wound, wherein the red circle indicates the position of the MSCSMs and the yellow circle indicates the position of the wound, according to an embodiment of the subject invention.

FIG. 6B showing a table of the steps of the guided delivery processes of MSCSMs towards the bile duct, wherein the delivery process can be divided into four stages; FIG. 6C showing Stage 0: delivery of the MSCSMs by the catheter equipped on an endoscope through the throat to the stomach and finally reaches the intestine; FIG. 6D showing Stage 1 and Stage 2: magnetic actuation of the MSCSMs in the intestine into the entrance of the bile duct under real-time tracking of the endoscope; FIG. 6E showing Stage 3: magnetic navigation of the MSCSMs inside the bile duct under real-time tracking of ultrasound (US) imaging; FIG. 6F showing a table of the deployment/delivery distance at each stage and the time spent, according to an embodiment of the subject invention.

DETAILED DISCLOSURE OF THE INVENTION

Figure 1A:
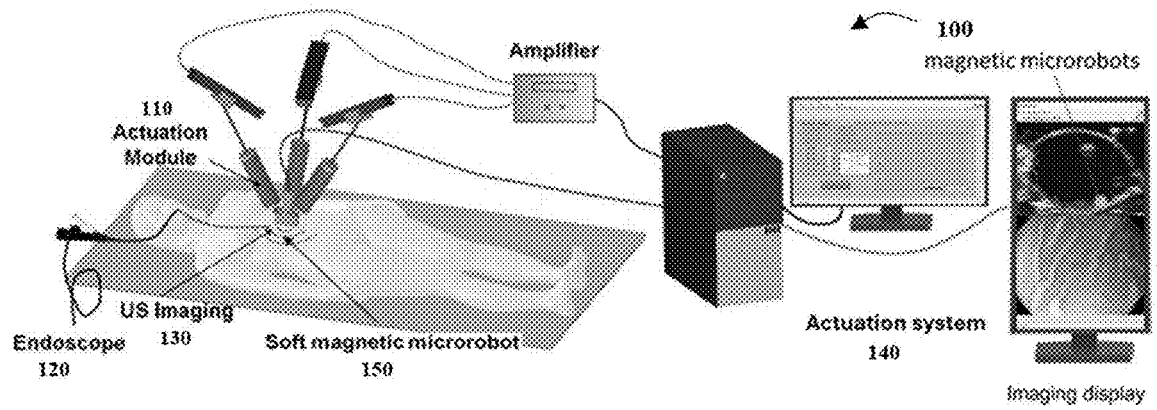
FIGS. 1A-1E are schematic representations of the integrated robotic system for rapid endoluminal delivery of microrobots to deep and narrow space, FIG. 1A showing the endoscope and US imaging-guided delivery of soft microrobots (i.e., MSCSMs) for targeted therapy in hard-to-reach regions.

The field of the invention is related to an integrated robotic system and methods for remote delivery and tracking of microrobots in clinical applications. Particularly, the systems integrate multiple clinical tools and imaging techniques to enable active and rapid delivery of magnetic miniature robots towards the deep and narrow space at a whole-body scale. The delivery process can be divided into two stages—a long-range delivery and a precise magnetic actuation. The long-range delivery is the delivery of the miniature robots by a catheter or an endoscope to a region near the targeted site, avoiding a direct contact with the complex fluidic environment and facilitating the rapid passing through multiple biological barriers in organs/tissues. After the long-range delivery, the precise magnetic actuation is configured to navigate the miniature robots into the targeted site by an external magnetic field. The imaging system is changed to a different system, as the original system cannot track the miniature robots once they enter a deeper or narrower region.

In one embodiment, the integrated robotic system is a hysteroscopy-assisted magnetic actuation with a dual imaging system. Biodegradable microrobotic swarm loaded with anti-adhesion drugs is delivered by a catheter via a hysteroscope to the location nearby the intramural, which is the opening of fallopian tubes, under the observation of hysteroscope. Then, the magnetic microrobots are gathered to a swarm and steered towards the intramural by the external magnetic fields. Next, once the microswarm enters the fallopian tubes, ultrasound imaging by a laparoscopic ultrasound probe is applied to track the location of microrobotic swarm. The microrobotic swarm navigates to the location near the obstruction in intramural and isthmus. After the microswarm reaches the targeted region, the microrobots will be dispersed by external magnetic fields, covering 1-2 cm around the obstruction region.

In one embodiment, the integrated robotic system is an endoscopy-assisted magnetic actuation with a dual imaging system (EMADIS) and the magnetic miniature robots are soft and resilient magnetic stem cell spheroid microrobots (MSCSMs) which are formed by 3D self-assembly of stem cells doped with a small number of magnetic particles. In the EMADIS, the endoscope offers an "express lane" for the MSCSMs to avoid direct contact with the complex fluidic environments and facilitates the rapid passage through multiple biological barriers in organs and tissues. The magnetic field actuation guides the high-precision delivery of the MSCSMs to the targeted position after the endoscopic deployment. Moreover, the endoscopic view and ultrasound imaging track the entire delivery process. As a result, the EMADIS enables the rapid and high-precision delivery of soft microrobots in real-time for the targeted therapeutic intervention of hard-to-reach regions, which are inaccessible and even invisible by means of conventional endoscopes and medical robots.

When the term "about" is used herein, in conjunction with a numerical value, it is understood that the value can be in a range of 90% of the value to 110% of the value, i.e. the value can be +/−10% of the stated value. For example, "about 1 kg" means from 0.90 kg to 1.1.

Reference will be made in detail to exemplary embodiments of the present invention in the following. The objects, characteristics, advantages and methods of the present invention will be more clearly understood through the drawings and following description but are by no means limited to the drawings and following description.

In the following embodiments of the subject invention, a bile duct is used as an example for a demonstration of the deep and narrow space to which the microrobots are delivered by the integrated robotic system. The bile duct is an important and narrow channel with a diameter of about 0.6~0.8 cm of a human body that connects the duodenum with the liver, spleen, and gallbladder. Controlled delivery through the bile duct is of great significance for the therapeutic functions of multiple organs through a minimally invasive manner.

Endoscopy-Assisted Magnetic Actuation with a Dual Imaging System (EMADIS)

Referring to FIG. 1A, the integrated robotic EMADIS 100 for a rapid endoluminal delivery of soft microrobots comprises a magnetic actuation unit 110 for remote magnetic control of the microrobots having sizes in millimeter, micrometer or nanometer scales, an endoscope unit 120, and one or more imaging unit 130 such as a ultrasound (US) imaging unit for tracking and capturing images of processes of the soft microrobots moving in different body parts during the delivery of soft microrobots in a duct such as a bile duct, an electromagnetic actuation system 140 for delivering the soft microrobots to hard-to-reach regions for the targeted therapy, and one or more soft magnetic microrobots 150 with various functionalities.

Figure 1B:
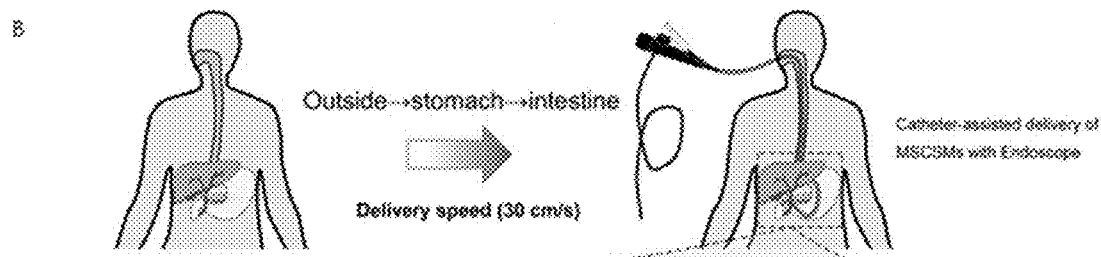
Figures 1C, 1D, 1E:
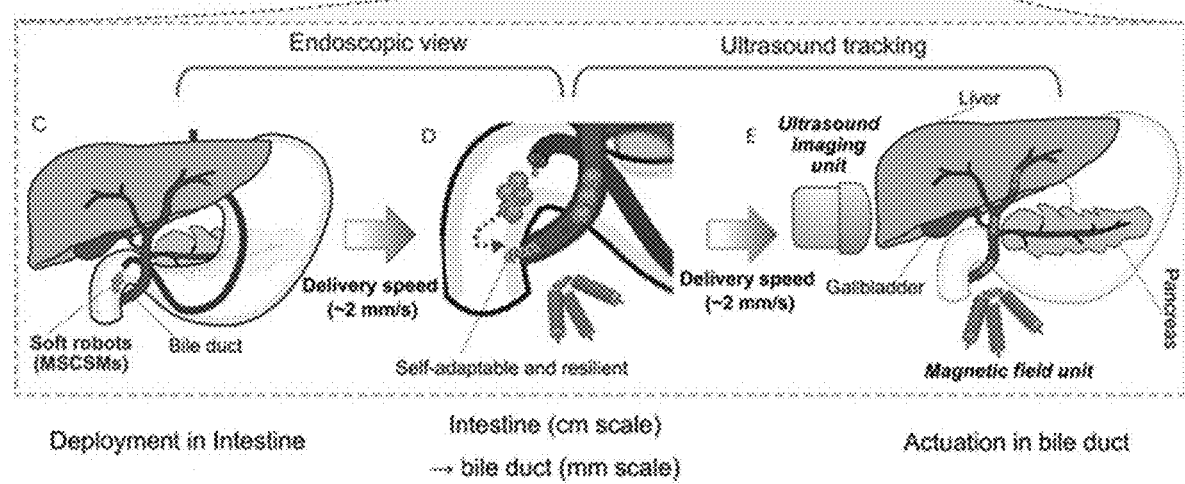

FIGS. 1B-1E illustrate one exemplary application of the integrated robotic EMADIS 100 for a rapid endoluminal delivery of soft microrobots in an imaging-guided delivery process. The soft microrobots can be injected in a controlled and minimally invasive manner to a region located close to the targeted site as shown in FIG. 1B. The subsequent navigation of the microrobots will then rely on magnetic actuation, with real-time tracking, by means of the endoscopic view as shown in FIGS. 1C and 1D. The tethered endoscope shows a limited accessible region inside the organism and the untethered microrobots released from the endoscope significantly extend the treatment area of the system. More importantly, while the targeted site is hidden in a region inaccessible and invisible by the endoscope, the microrobots can be further tracked by the US imaging technique to reach the destination including inside narrow ducts and confined cavities for therapeutic purposes, as shown in FIG. 1E.

The delivery process can be divided into two steps: a long-range delivery step and a precise magnetic actuation delivery step. First, in the long-range delivery step, the soft microrobots 150 are delivered by the endoscope unit 120 having a catheter and an endoscope imaging device to a region near the targeted site to avoid direct contact with the complex fluidic environment and to facilitate rapid passing through multiple biological barriers in organs/tissues. For example, the long range or long distance can be about 50-150 cm. The endoscope imaging is configured to track and capture images of processes of the soft microrobots delivery step. Then, in the precise magnetic actuation delivery step, the magnetic actuation unit 110 is configured to guide the microrobots to the targeted site by applying magnetic forces of magnetic fields. For example, the precise magnetic actuation has a resolution of mm scale. Next, a second imaging device such as a ultrasound (US) imaging unit is employed to track and capture images of processes of the soft microrobots delivery, as it is difficult for the endoscope imaging device to track the microrobots once they enter a deeper or narrower region, allowing the high-precision delivery of the microrobots to the targeted position after the endoscopic deployment.

Formation of Soft Microrobots

Referring to FIGS. 2A-2G, a self-assembly process of stem cells and magnetic particles into a three-dimensional (3D) soft magnetic stem cell spheroid microrobot 150 without any rigid scaffold is illustrated. The biohybrid microrobot 150 comprises magnetic particles immobilized intercellularly.

Figures 2A, 2B, 2C:
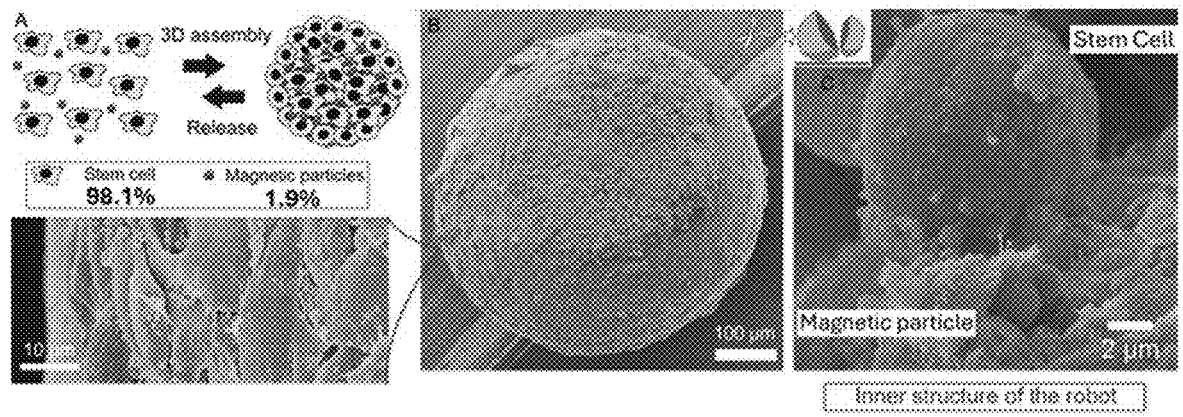
FIGS. 2A-2G are schematic representations of formation, characterization, and viability assessment of live stem cell spheroid microrobots, FIG. 2A showing the self-assembly process of stem cells and magnetic particles into a three-dimensional (3D) magnetic stem cell spheroid microrobot (MSCSM)
Figure 2D:
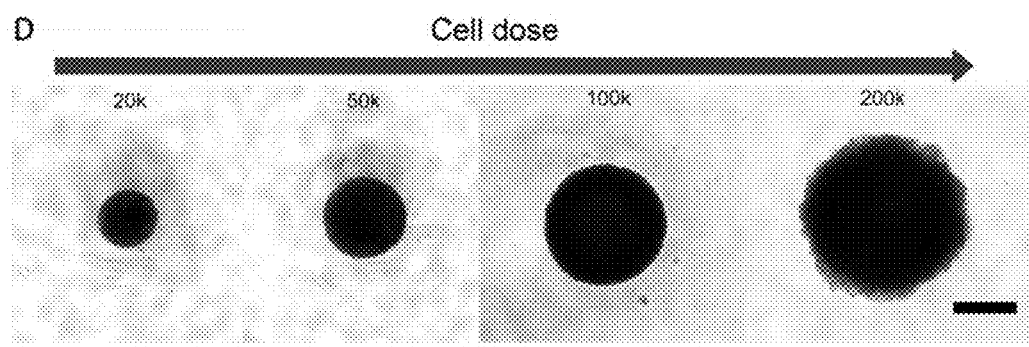
Figure 2E:
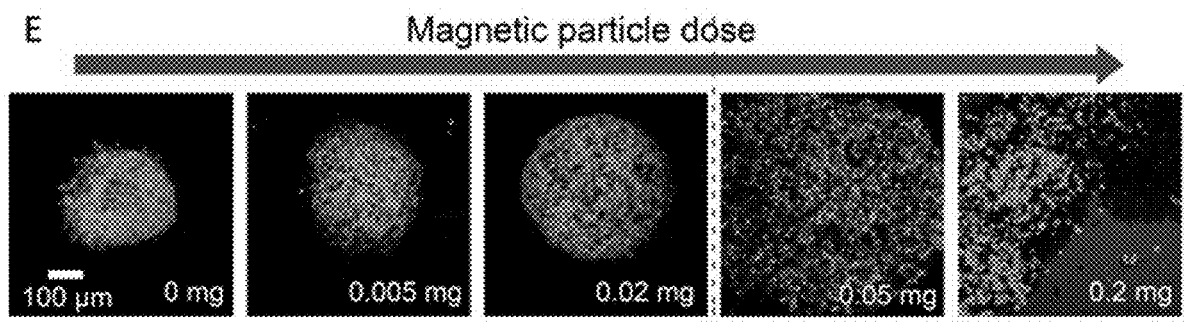
Figure 2F:
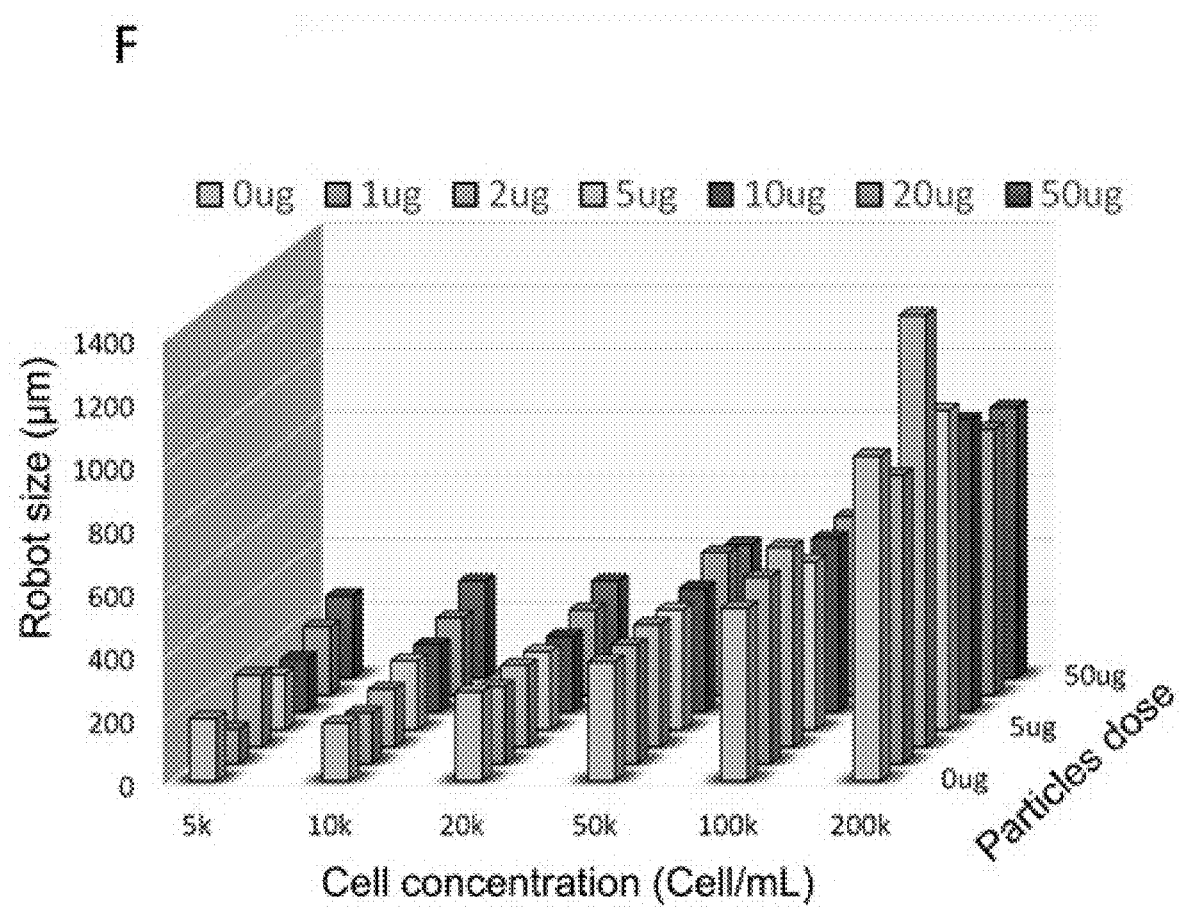
Figure 2G:
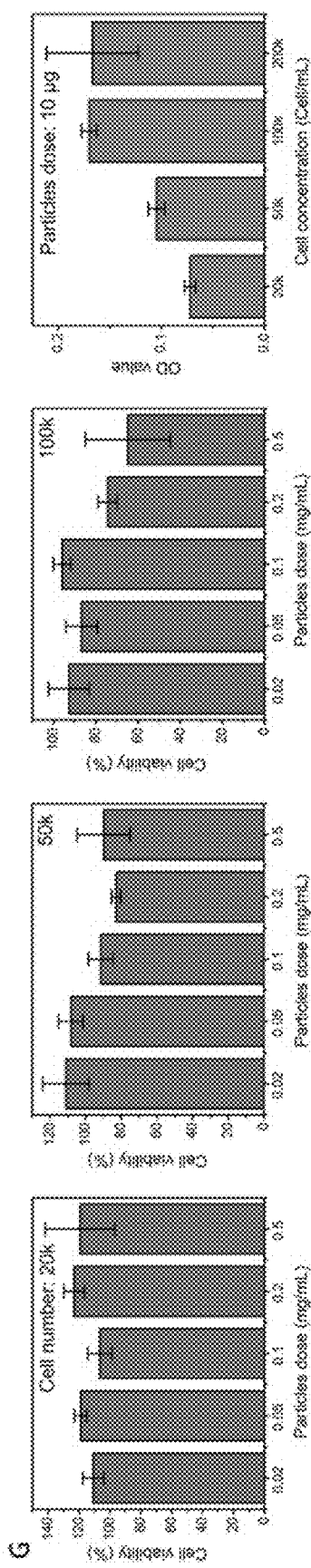

The microrobots are formed through a co-culture process of stem cells and polydopamine coated magnetic iron particles on a non-adhesive surface, forming the spherical structure, as shown in FIGS. 2A-2B. After the cutting process of a magnetic stem cell spheroid microrobot (MSCSM), the inner distribution of stem cells and magnetic particles, for example, about 2-3 µm, are inspected by scanning electron microscopy (SEM) and results shown in FIG. 2C indicates that the magnetic particles have an average particle size of approximately 3 µm. The magnetic saturation value is measured to be about 198 emu/g, which is more than twice the magnetic saturation value of commonly prepared magnetite nanoparticles. The excellent magnetism facilitates the efficient actuation and delivery of stem cells with an ultralow dose of magnetic particles. The spheroid microrobots remain stable and closely packed at the relatively low particle dose, but become unstable when the particle dose exceeds approximately 0.02 mg as shown in FIG. 2E. A high particle dose is disadvantageous for the formation of the MSCSMs, given that the high particle dose may weaken the interactions between the stem cells. The size of the MSCSMs is mainly determined by the initial stem cell concentration as shown in FIGS. 2D and 2F. The volume percent of the stem cells in a MSCSM with cell number=100 k, particles amount=10 µg is calculated to be approximately 98.1%, demonstrating the ultralow number of magnetic particles inside the MSCSMs. The outstanding cell viabilities of the MSCSMs are verified by means of the 3-(4, 5-dimethylthiazol-2-yl)-5-(3-carboxymethoxyphenyl)-2-(4-sulfophenyl)-2H-tetrazolium (MTS) assay as shown in FIG. 2G. The MSCSMs can be stored in batches for further use, with high cell viability, via a dynamic rotating culture system (not shown). The geometry and component of the MSCSMs can be further adjusted in a configurable manner by the differentiation or co-culture of multiple MSCSMs.

Figure 3A:
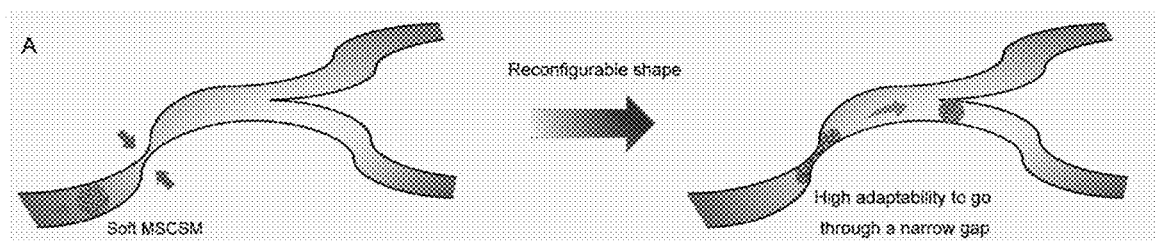
FIGS. 3A-3F are schematic representations of softness and elasticity of MSCSMs, FIG. 3A showing the reconfigurable motion of the MSCSM while passing through a narrow channel with a width smaller than the diameter of the MSCSM.

Since the MSCSMs are formed by the assembly of the stem cells with a small number of magnetic particles, the soft microrobots exhibit excellent elasticity and softness, and can be actuated to pass through the complex environment in reconfigurable manner as shown in FIG. 3A. When being compressed, the MSCSMs can recover to their original shapes and structures after the compression is retracted.

Figure 3B:
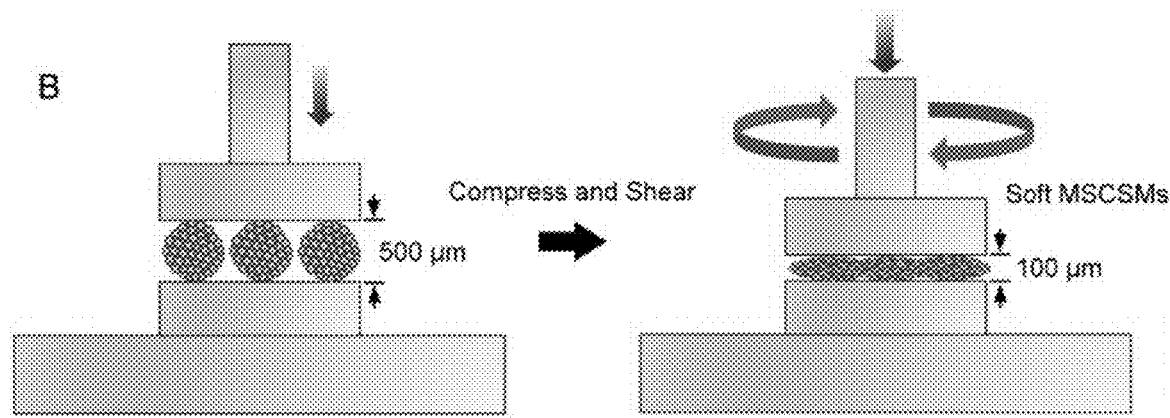
Figure 3C:
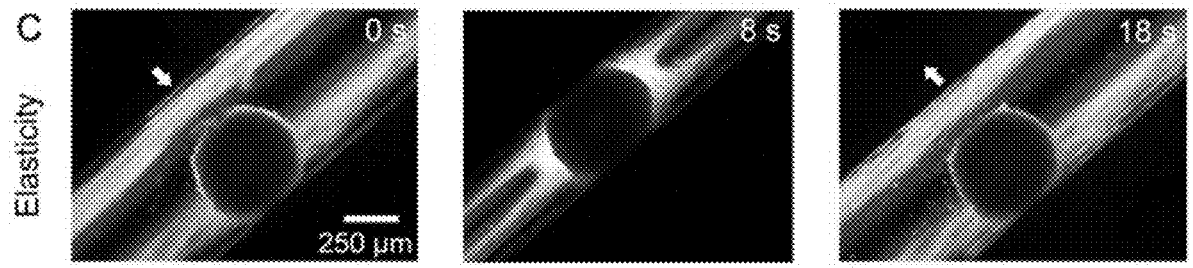
Figure 3D:
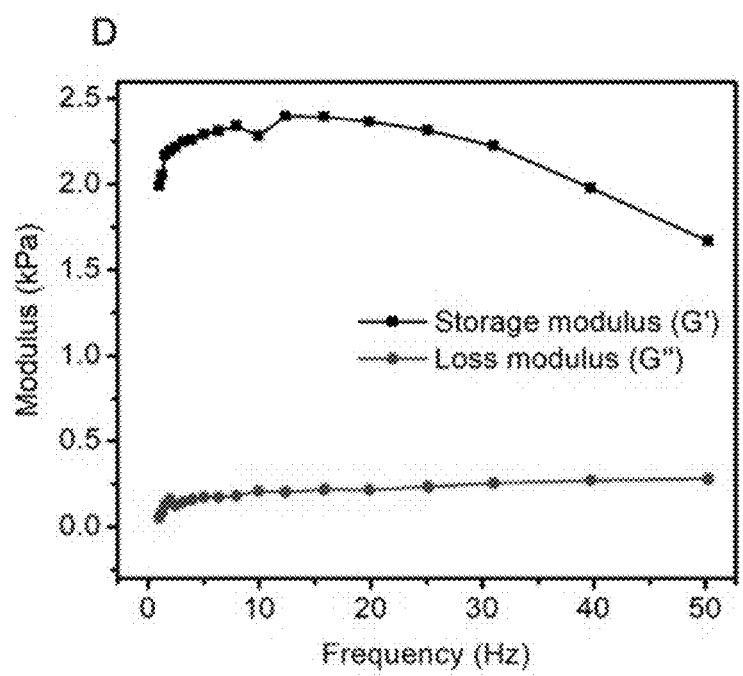
Figures 3E, 3F:
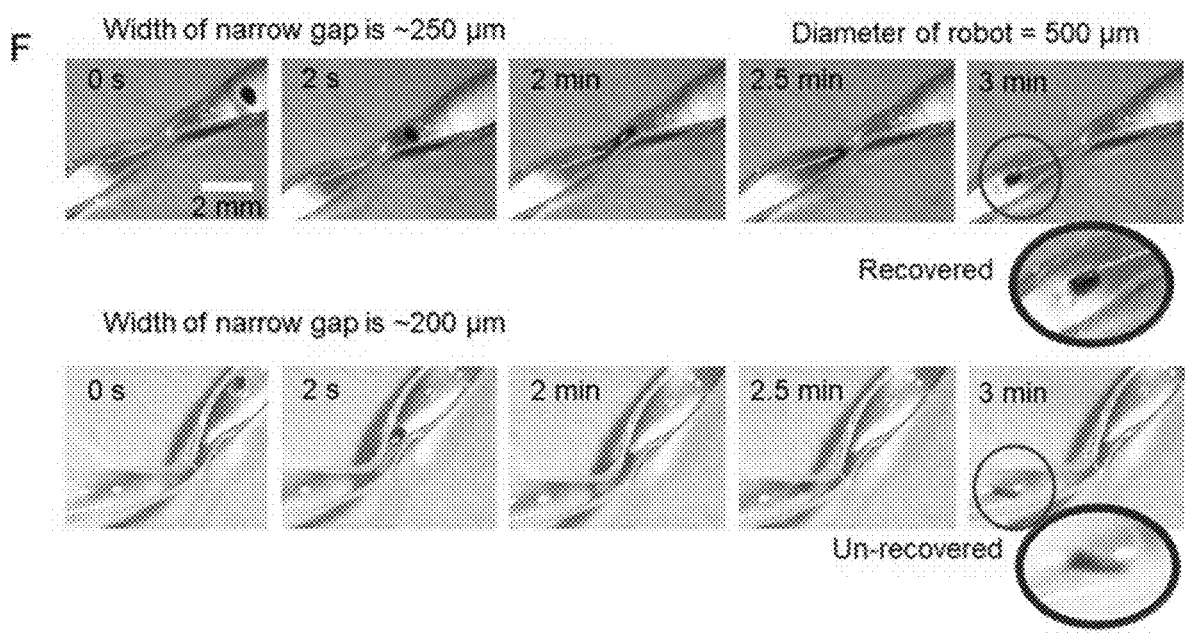

Although the MSCSMs can be compressed on demand as shown in FIG. 3B, they also can recover their shape after the compression is retracted as shown in FIG. 3C. The storage modulus and loss modulus are measured to be approximately 2.0 and 0.2 kPa, respectively as shown in FIG. 3D. Compared with daily materials and biological samples of FIG. 3E, the modulus of the MSCSMs is smaller than that of human facial skin, exhibiting exceptional softness of the MSCSMs. Moreover, the MSCSMs show elasticity and deformability during the navigation in the complex 3D channel. As illustrated in FIG. 3F, when the MSCSMs pass through a narrow channel with a width smaller than the diameters of the MSCSMs, the shapes of the soft microrobots are automatically transformed to adapt to the narrow gap and pass through the narrow gap in a reconfigurable manner. For a narrow channel with an inner width of about 250 µm, which is about half of the diameter of the soft microrobots, the soft microrobots can recover their shapes after the reconfigurable passing process. A further decrease of the channel width may induce irrecoverable shapes of the soft microrobots, even though the soft microrobots may still maintain the intactness and cell viability for the magnetic navigation with high controllability and precision.

In one embodiment, the soft microrobot 150 is formed by a three-dimensional (3D) self-assembling of stem cells doped with a small amount (for example, less than 2%) of magnetic particle intercellularly, making the microrobot extremely soft and biocompatible with an elastic modulus even smaller than the human face skin. The softness and elasticity of the microrobot provide the microrobot with excellent adaptability to the surroundings by self-alternating of the structure with reconfigurable fashion. The stem cells may be harvested from the host so that the immune response can be minimized and even eliminated during the delivery and therapy.

The soft microrobots 150 are formed through a co-culture process of the stem cells and the biocompatible polydopamine coated magnetic iron particles on the non-adhesive surface. Stem cells and the magnetic particles spontaneously integrate and form a biohybrid tiny agent with spherical shape through a simple co-culture process. The spontaneously formed spherical structure facilitates the magnetic actuation capability.

The soft microrobot possesses highly saturated and compact cells arrangement with a maximum stem cell proportion of about 98% in volume. It also inherits the excellent softness and biocompatibility of live tissue with an elastic modulus even smaller than the human face skin, making the soft microrobot resilient and reconfigurable among the navigation inside the body. The formation of the soft microrobots has no adverse effects with respect to cell viability, cell proliferation and differentiation capacity on the stem cells. Moreover, the natural camouflage of the soft microrobots by the surface stem cells shows the potential in the suppression of immune response effectively.

In Vitro Delivery, Release, and Therapy

Figure 4A:
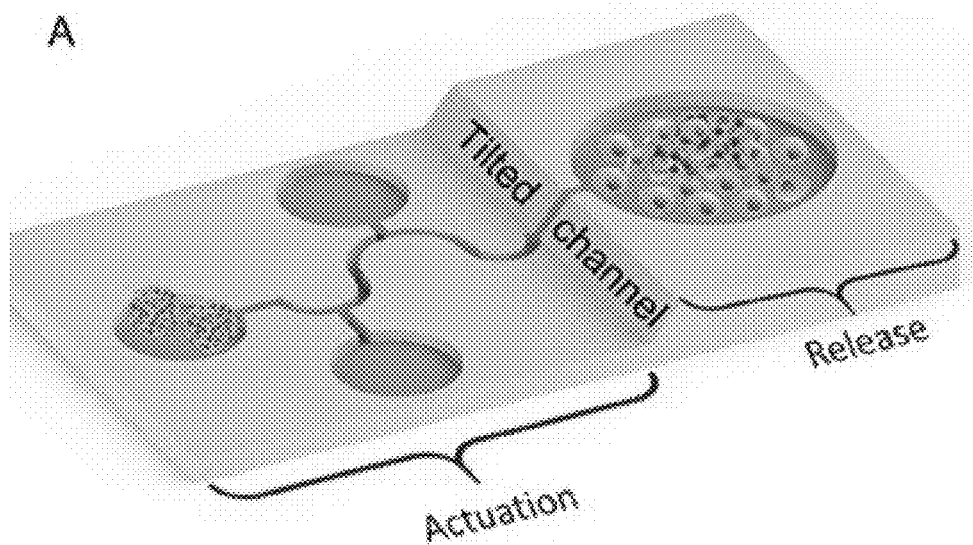
FIGS. 4A-4N illustrate in vitro delivery, release, and therapeutic effects of the MSCSMs, FIG. 4A showing schematic representations of the targeted delivery, release, and therapy of the MSCSMs under a magnetic field.
Figure 4B:
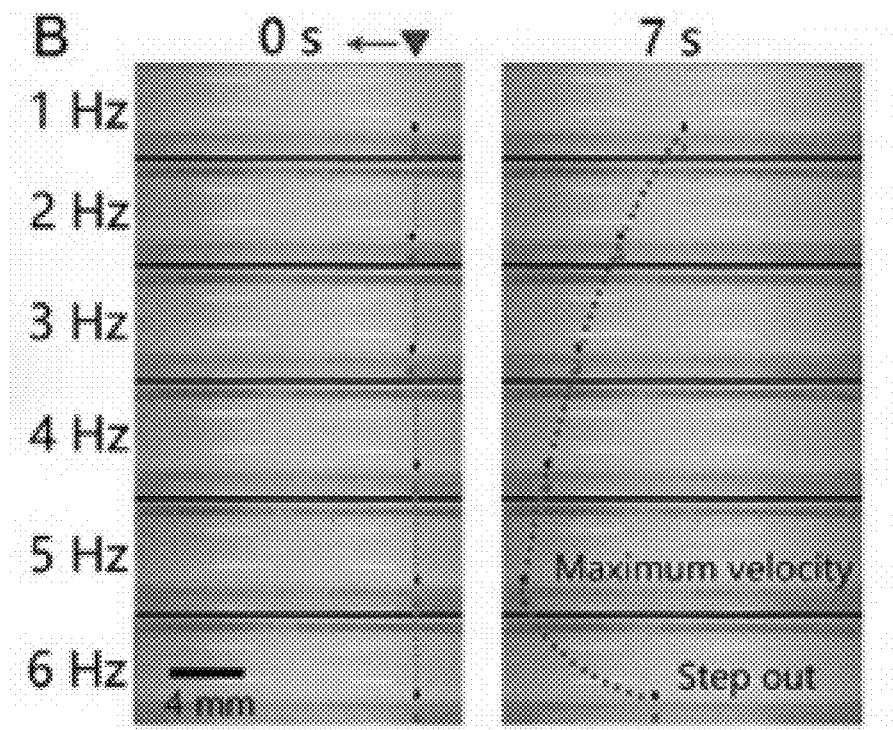
FIG. 4B showing optical images of the actuation of the MSCSMs with different frequencies (field strength is 10 mT, 90°)
Figure 4C:
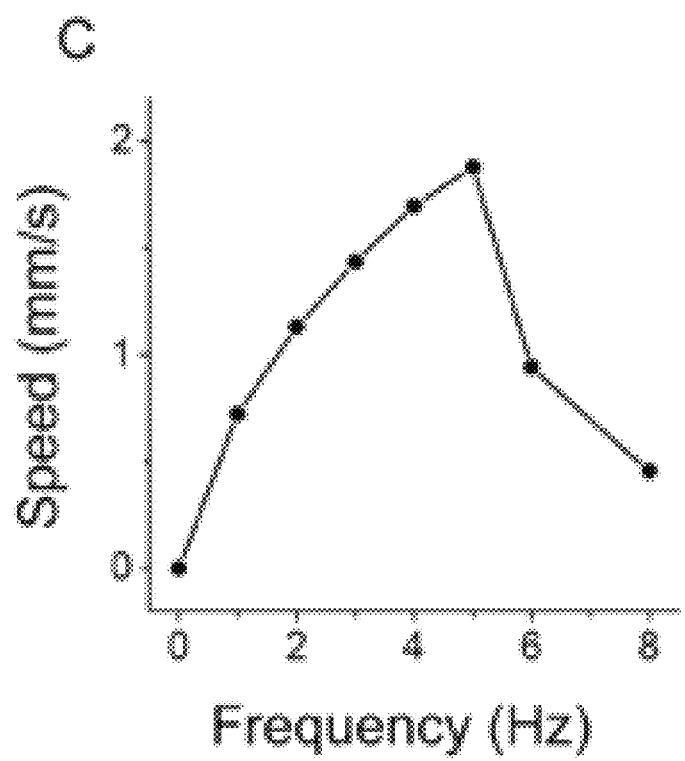
FIG. 4C showing relationships between the speed of the MSCSMs and the frequency of the magnetic field (field strength is 10 mT, 90°)
Figure 4D:
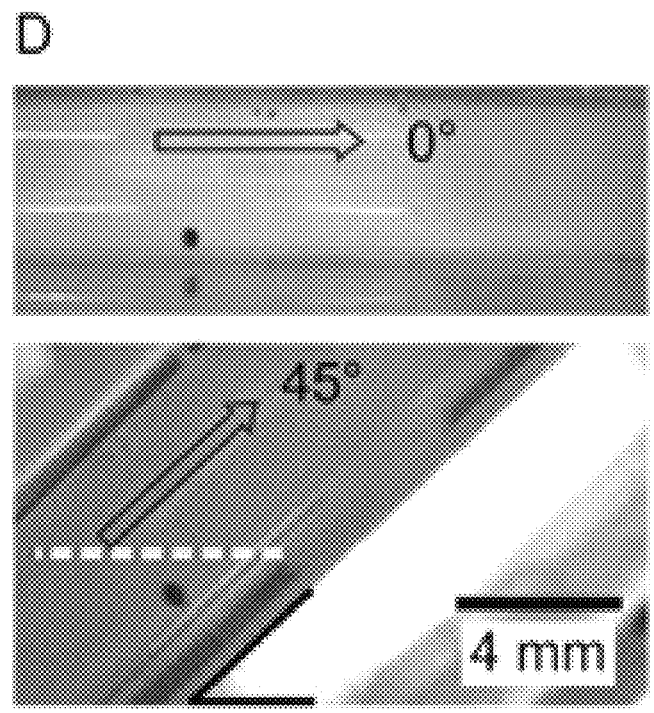
FIG. 4D showing optical images of the actuation of MSCSMs on a tilted surface.
Figure 4E:
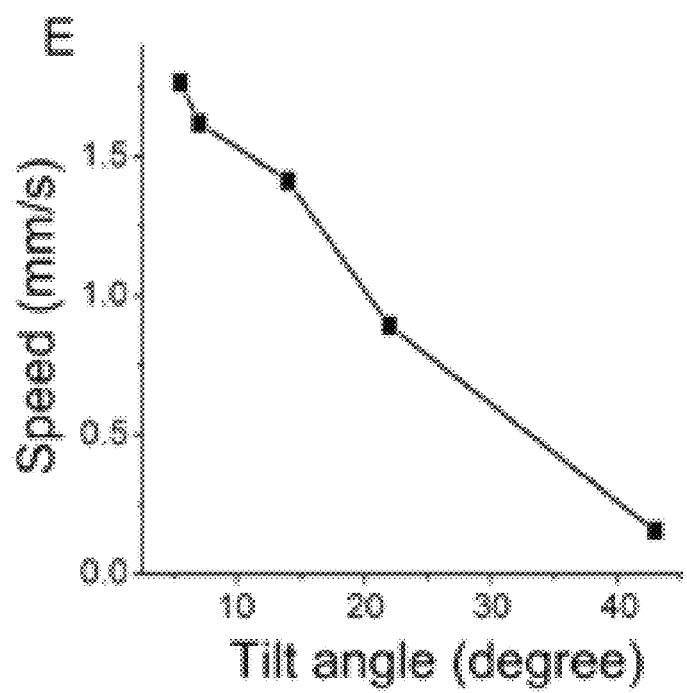
FIG. 4E showing relationships between the uphill speed of the MSCSMs and tilt angle (10 mT, 5 Hz, 90°)

The in vitro delivery and release process is illustrated in FIG. 4A. The delivery was performed under a magnetic actuation process. After the MSCSMs are delivered to the targeted site, the incubation process is carried out to release the stem cells. FIG. 4B shows the magnetic actuation process of the MSCSMs under different field frequencies. The maximum speed was measured to be 1.9 mm/s with a step-out frequency of 5 Hz as shown in FIG. 4C. The MSCSMs can also be actuated along a tilted surface as shown in FIG. 4D. As the tilt angle of the surface increases, the speed of the MSCSMs decreases accordingly, wherein strength is 5 mT and frequency is 5 Hz, as shown in FIG. 4E. The MSCSMs can climb a tilted surface with a tilt angle of up to approximately 45°. The results suggest that the MSCSMs can navigate complex surface topographies having a plurality of surfaces and curvatures.

The stem cells in the MSCSMs are relatively stable during extended navigation. In one embodiment, after one hour of actuation, the remaining fluorescent intensity of the MSCSM is 89.2% of its initial intensity. Further, after arriving at the desired position, the MSCSMs can be fixed to the position, on-demand, against strong flows of fluid up to about 108 mm/s.

Figure 4F:
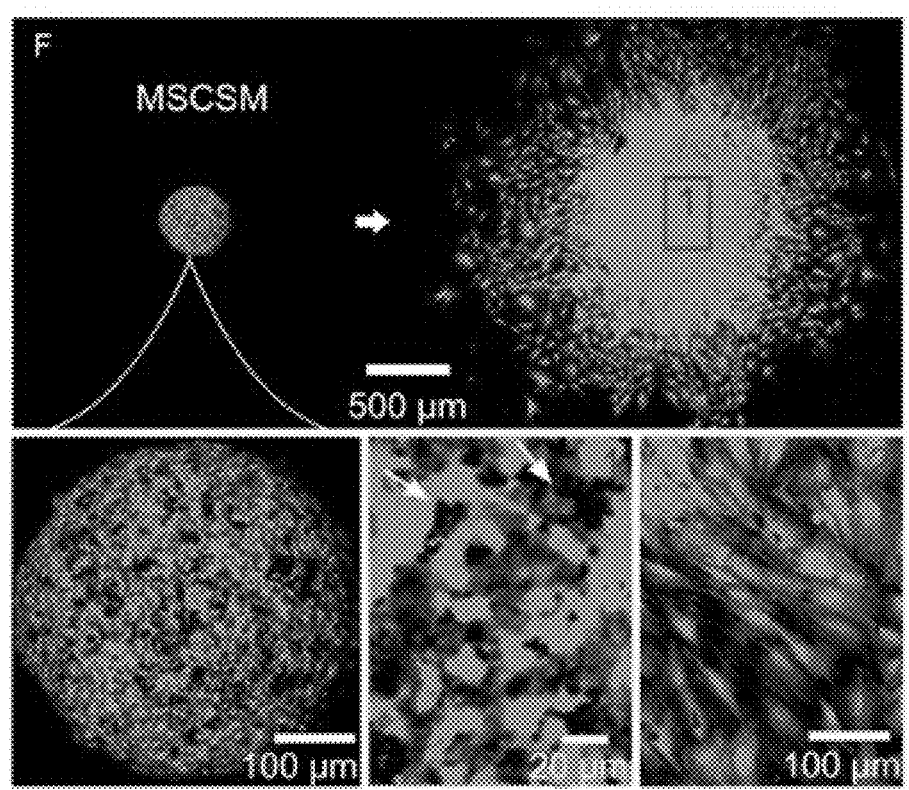
FIG. 4F showing the CLSM images of an MSCSM before and after the release process, wherein the enlarged CLSM images show the MSCSM before spreading, and the center and edge of the MSCSM after spreading process, respectively.
Figure 4G:
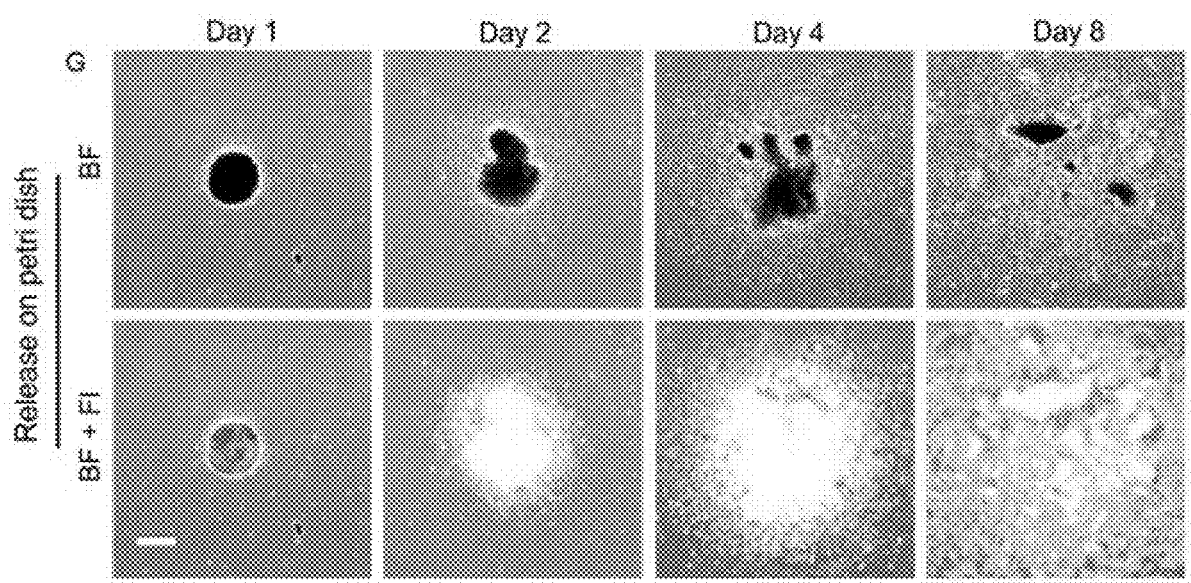
FIG. 4G showing BF images of the delivery and spreading process of the MSCSMs at different times.
Figure 4H:
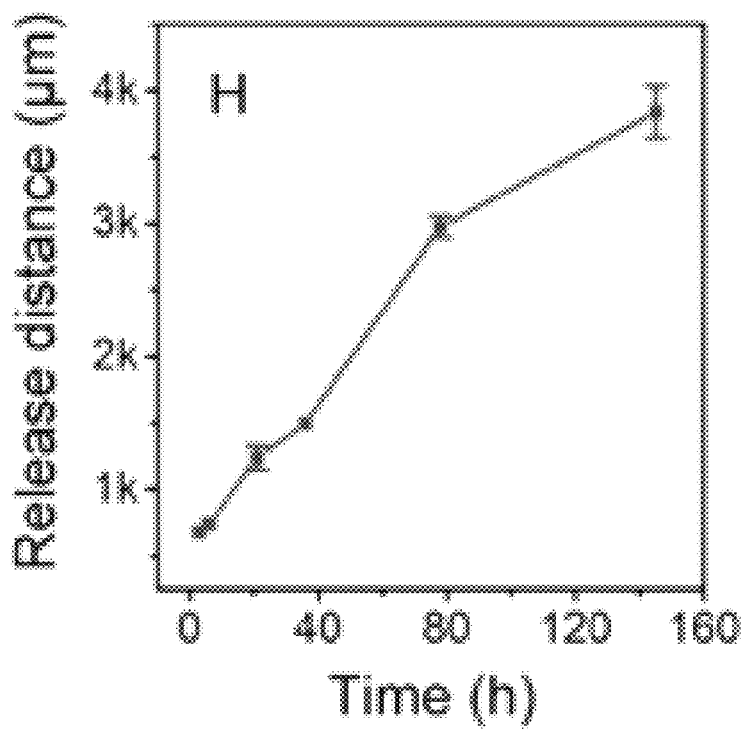
FIG. 4H showing relationships between the spreading size of the MSCSM at different times.
Figure 4I:
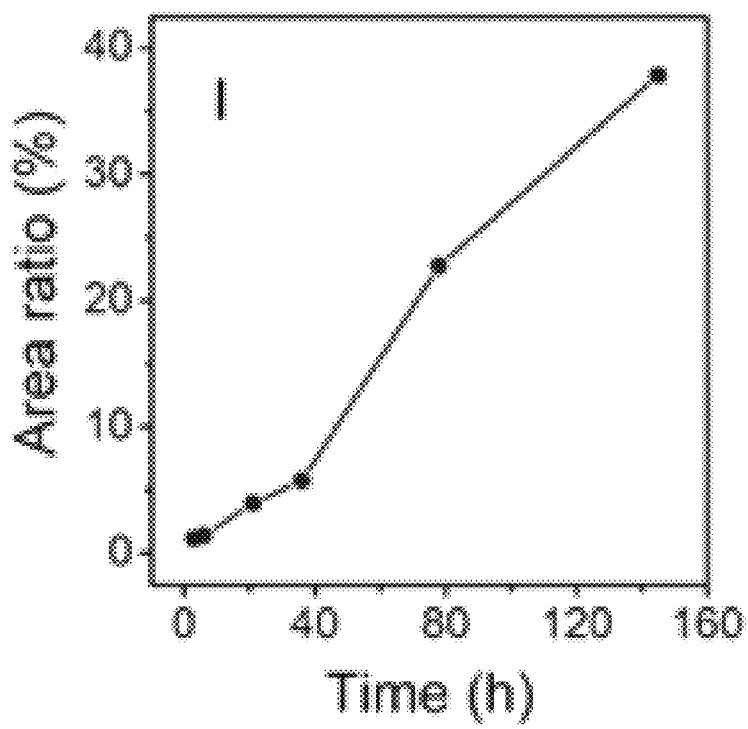
FIG. 4I showing relationships between the area ratio of the MSCSM before and after spreading at different times.
Figure 4J:
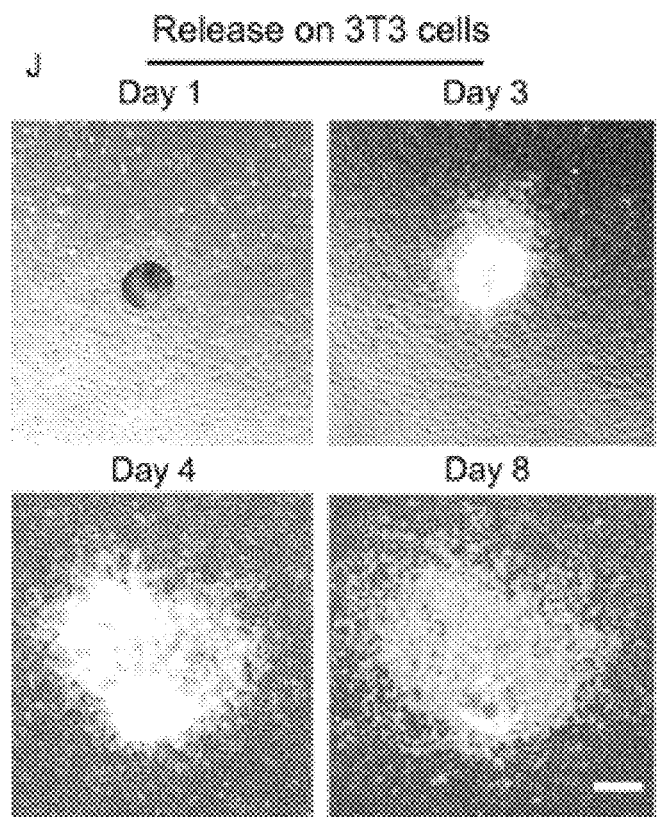
FIG. 4J showing merged images of the BF and fluorescent images of the spreading process of MSCSMs on the 3T3 cell surface at different times.
Figure 4K:
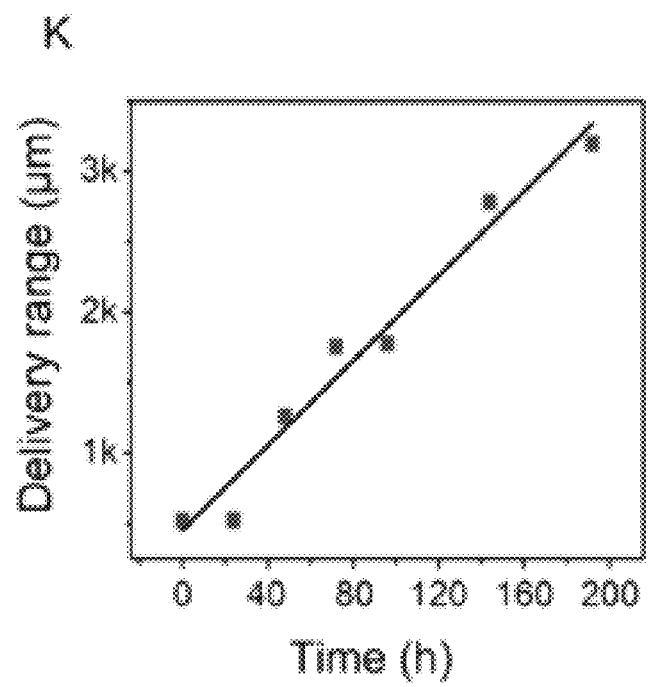
FIG. 4K showing delivery range of MSCs from the MSCSM on 3T3 cell film.

After the delivery, the stem cell is capable of performing controlled release via a cell proliferation process. The CLSM images in FIG. 4F show the typical release process of an MSCSM and two adjacent MSCSMs, respectively. The local details suggest that the stem cells of the MSCSMs migrated outward, and the configuration of cells at the outer ring changed from an irregular shape to a spreading shape as shown in FIG. 4F. The quantitative relationship between the release distance, released area ratio, and the culture period are illustrated by FIGS. 4G-4I. It is noted that both the release distance and the released area ratio linearly increase with time.

Figure 4L:
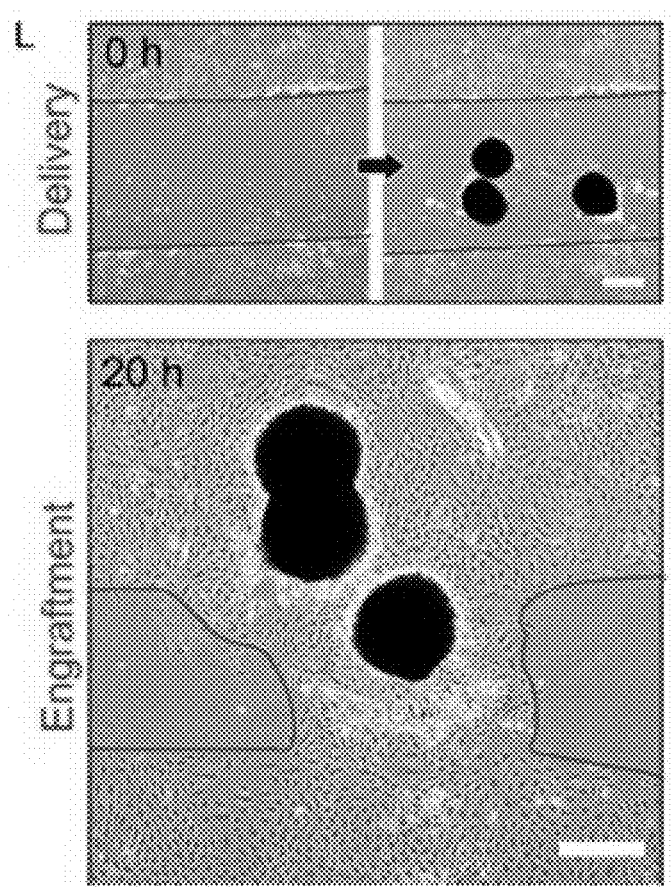
FIG. 4L showing BF images of the delivery of MSCSMs to the scratched area and proliferation of MSCSMs on the scratches of 3T3 cell monolayers.
Figure 4M:
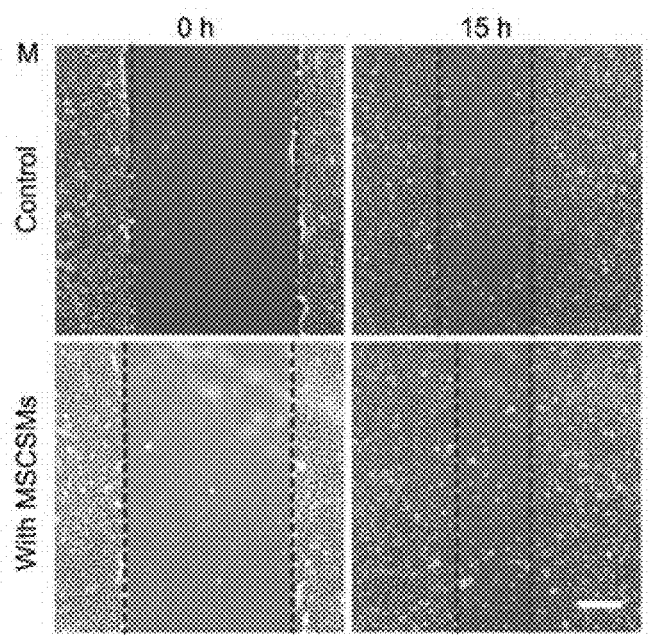
FIG. 4M showing BF images of the healing of the scratches on 3T3 cell films with and without MSCSMs.
Figure 4N:
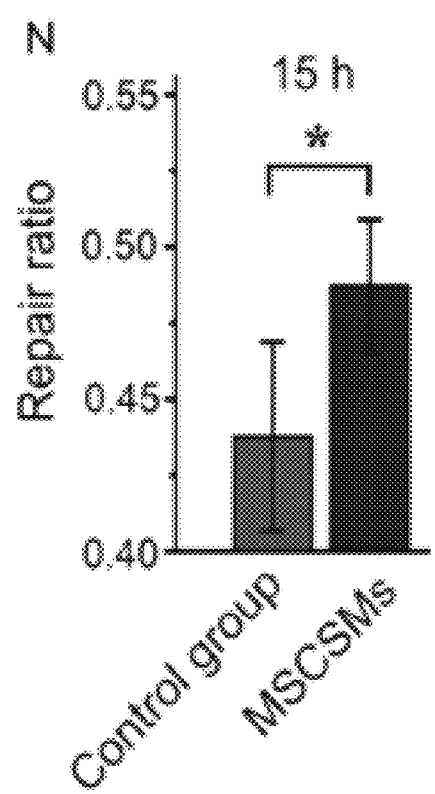

Moreover, the therapeutic effect of stem cell therapy mainly depends on the effect of released bioactive molecules such as various growth factors and in situ engraftment or transdifferentiation. Therefore, these two abilities of MSCSMs are tested to evaluate their therapeutic effects. The in vitro therapeutic effect is verified by the targeted delivery of the MSCSMs to the scratched 3T3 surface as shown in FIG. 4J-4M. To test the ability of in situ engraftment of MSCSMs, the MSCSMs demonstrate the ability of release and proliferation on the 3T3 monolayer. As demonstrated in FIGS. 4J-4K, the in situ engraftment area on the 3T3 cells increased linearly with time. While the MSCSMs are actuated to the scratched area of a 3T3 cell film, the MSCSMs show exceptional repairing ability by means of engraftment as shown in FIG. 4L. To examine the effect of the secretome of MSCSMs on cell migration, an in vitro scratch assay is conducted with a 3D-printed channel cultured with fibroblast 3T3 cells as shown in FIG. 4M. The results also indicate that the MSCSMs facilitate cell migration and, consequently, improve healing significantly ($P<0.05$) after 15 hours, when compared to the control group as shown in FIGS. 4M and 4N. Therefore, both the engraftment and secretome of the MSCSMs have been demonstrated to show potentials in tissue healing.

Endoscopy-Assisted Delivery in Large Cavities

Figure 5A:
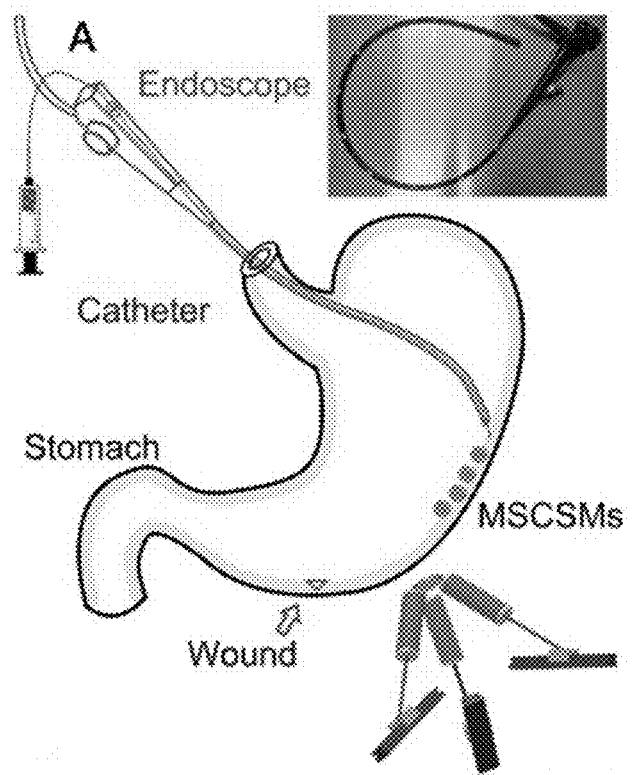
FIGS. 5A-5C are schematic representations of endoscopy-assisted delivery of MSCSMs to the wound in a pig's stomach, FIG. 5A showing the experimental setup, wherein the inset shows a photograph of the clinical upper gastrointestinal endoscope, FIG. 5B showing that at first the endoscope enters the pig's stomach, and a catheter passes through the channel of the endoscope and reaches inside the stomach, MSCSMs are next delivered to the stomach via a catheter by direct injection, the MSCSMs are then assembled via dynamic magnetic fields.
Figure 5B:
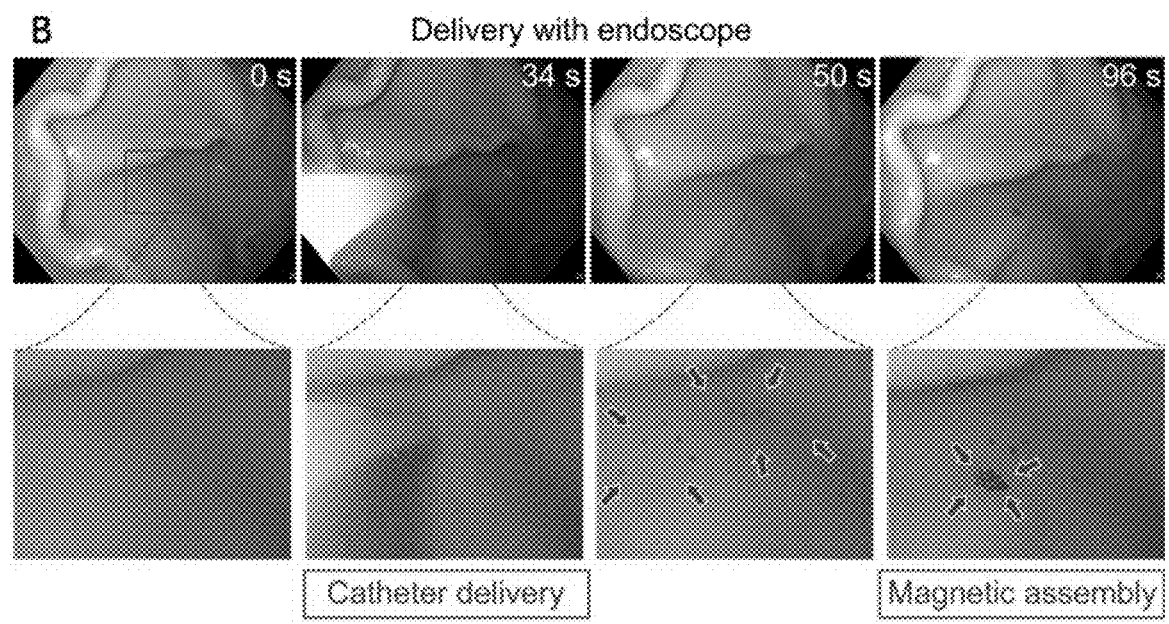
Figure 5C:
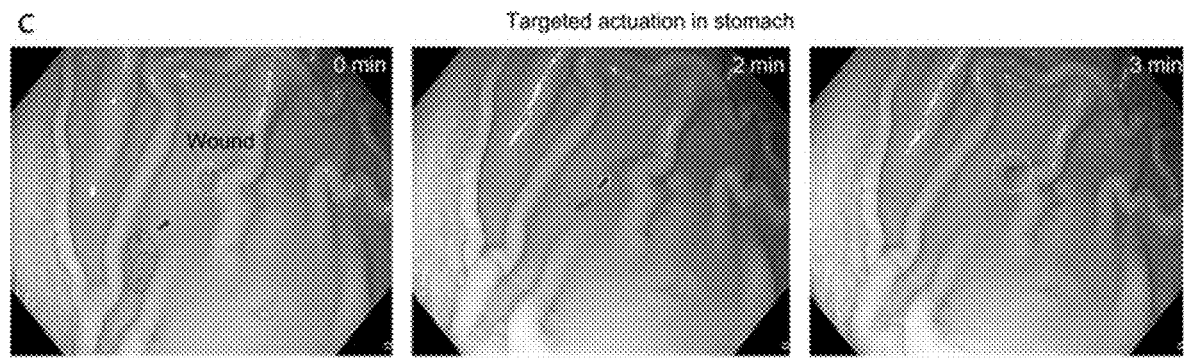

For delivery in large cavities, evaluations of the endoscopy-assisted delivery and high-precision actuation of MSCSMs to the wound site in the gastrointestinal (GI) tract is shown in FIG. 5A. The endoscopy-assisted delivery of MSCSMs is demonstrated within a pig's stomach with a clinical upper GI endoscope equipped with a 14G catheter as shown by the inset in FIG. 5A. The catheter in the endoscopy offers a harbor and "express lane" for the MSCSMs to avoid direct contact with the complex fluidic environments and the barriers among different organs and tissues. The catheter equipped inside the endoscope is capable of delivering large numbers of MSCSMs in the batch process. After the MSCSMs are delivered into the stomach, they are further guided by an external magnetic field toward the targeted region. The magnetic field can be used to gather the swarming MSCSMs into a confined area as shown in FIG. 5B. The remote actuation approach is capable of concentrating the injected MSCSMs and avoids loss of MSCSMs during the further actuation process. Moreover, the MSCSMs can be actuated on the mucosa layer under the external magnetic field towards the pre-induced wound as shown in FIG. 5C.

EMADIS for Image-Guided Delivery to Narrow Ducts and Small Cavities

Figure 6A:
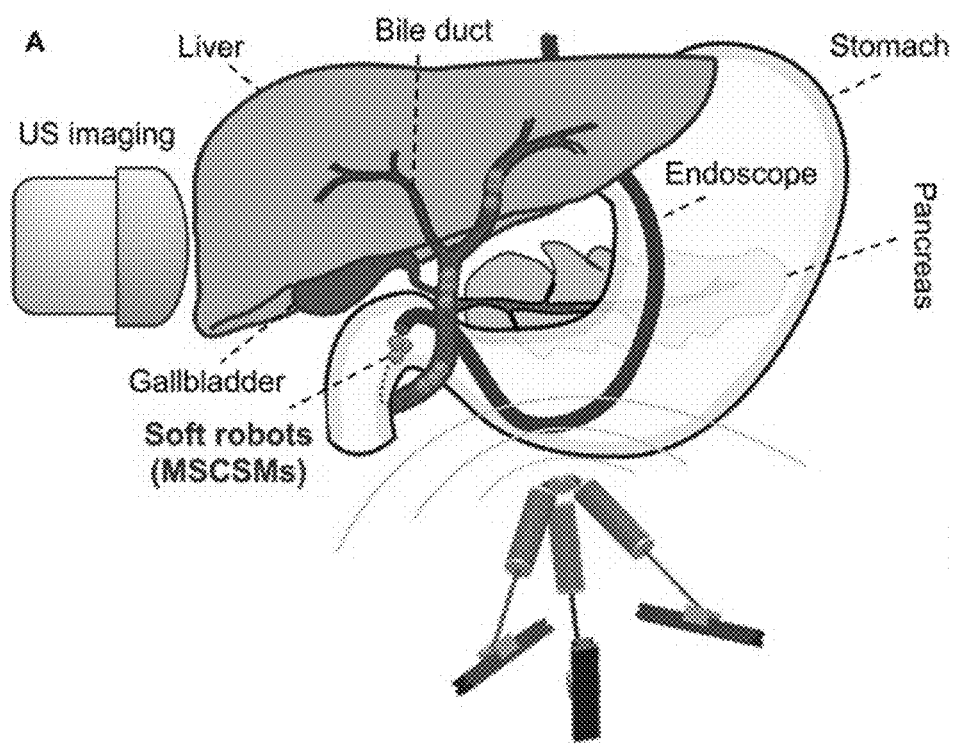
FIGS. 6A-6F showing the endoscopy-assisted magnetic actuation with a dual imaging system (EMADIS) enables the rapid delivery of the soft MSCSMs to the deep bile duct under combined imaging modalities in a real-time fashion, FIG. 6A showing the experimental setup.

For delivery to narrow ducts and small cavities, the EMADIS enables the rapid deployment and high-precision delivery of soft MSCSMs in real-time to hard-to-reach regions. The US imaging-guided actuations of a single MSCSM and multiple MSCSMs in vitro, and navigation of a swarm of MSCSMs in vivo, are evaluated. The bile duct is used as an example for demonstration of the deep and narrow space delivery of the MSCSMs by the EMADIS. The bile duct is an essential and narrow channel (with a diameter of 0.6-0.8 cm) that connects the duodenum with the liver, spleen, and gallbladder as shown in FIG. 6A. The EMADIS is employed to realize the minimally invasive peroral delivery of the MSCSMs into the bile duct precisely by means of magnetic control with real-time feedback from the combined imaging mode of endoscopy and US tracking.

Figures 6B, 6C:
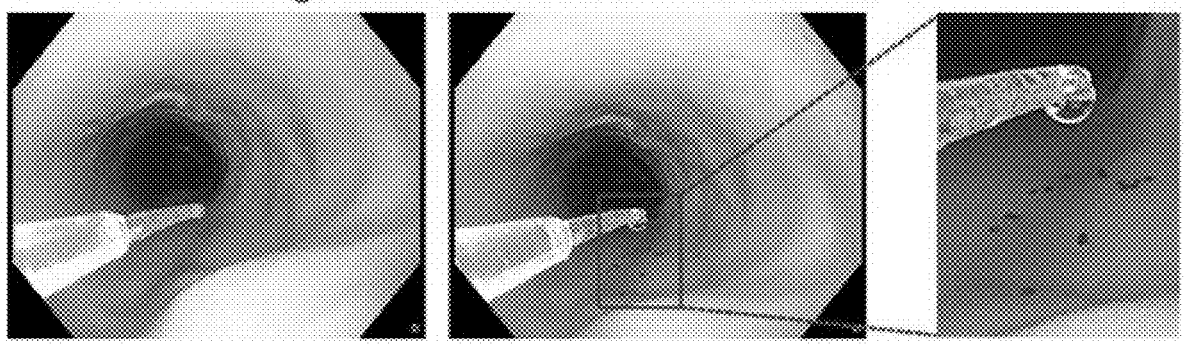
Figure 6D:
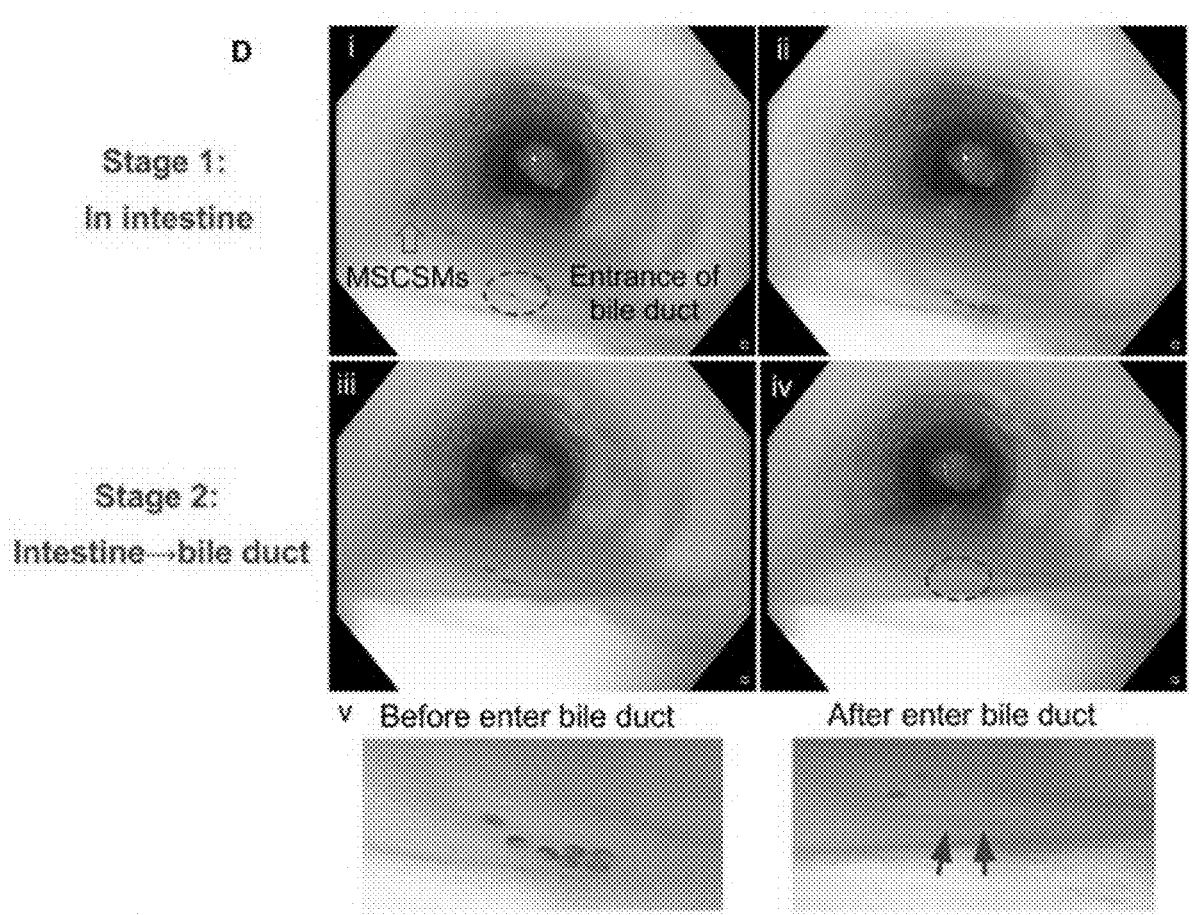
Figures 6E, 6F:
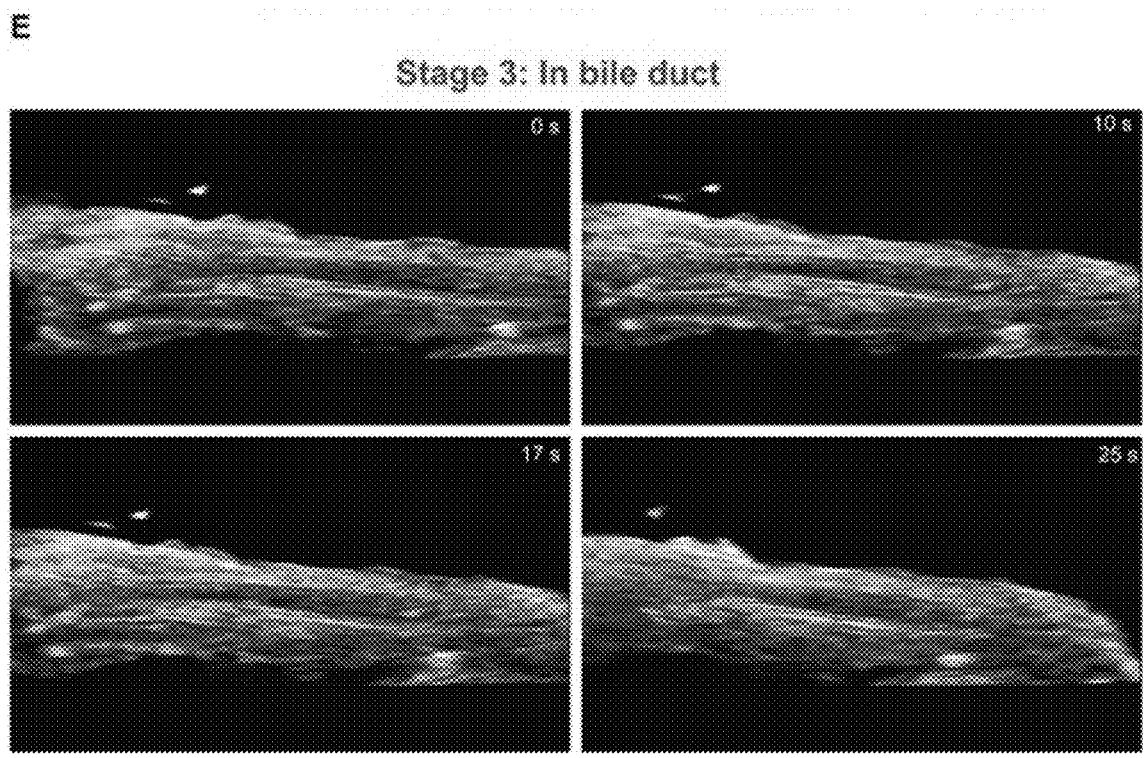

The delivery of MSCSMs by means of the EMADIS can be divided into four stages as shown in FIG. 6B. In Stage 0, the MSCSMs are deployed to the duodenum which is close to the stomach using the catheter with real-time monitoring by means of the endoscope as shown in FIG. 6C. Subsequently, under endoscopic monitoring, the released MSCSMs are actuated by a remote magnetic field towards the tiny entrance of the bile duct on the inner wall of the duodenum (Stage 1, as shown in FIG. 6D). Then, strong magnetic attractions are applied to pull the MSCSMs into the bile duct (Stage 2, as shown in FIG. 6D). After the MSCSMs enter the bile duct, the endoscope is unable to observe and track their trajectories, and the US imaging setup is used for further tracking and guidance of the translational motion of the MSCSMs (Stage 3). As shown in FIG. 6E, after switching the imaging mode in the bile duct, the MSCSMs can be magnetically driven to the gallbladder with real-time location feedback from the US imaging. The motion distances and time during each stage are estimated as shown in FIG. 6F and the delivery distance of MSCSMs may reach 100 cm during the entire process. However, the time spent on delivery can be controlled to be less than 8 min, demonstrating the time-efficient delivery across extended distances and over multiple organ barriers. As shown in the table of FIG. 6F, the speed of the MSCSMs inside the catheter of the endoscope is approximately 30 cm/s, which is two orders of magnitude higher than the maximum speed when the MSCSMs are under magnetic actuation. Therefore, maximizing the deployment distance by means of endoscopy is favorable to shorten the time required for the entire delivery process. High-precision magnetic actuation is performed after maximizing the reachable region of endoscope towards the targeted location. The combination of magnetic actuation, endoscopy, and US imaging modality offers the maximum application scope of the magnetic microrobots for in vivo applications at the whole-body scale.

Additionally, magnetic resonance imaging (MM) may be integrated with endoscopy for tracking and imaging the magnetic field-guided delivery of MSCSMs to organs and tissues. It is observed that the swarm of MSCSMs, in both the stomach and abdominal cavity, can be tracked by means of T2-weighted MM imaging under magnetic actuation. Unlike the US imaging, MRI is also applicable for those regions shielded by bone.

The aforementioned results suggest that the integration of clinical surgical tool, the microrobotic system, and the clinical imaging techniques, offer complementary advantages in the microrobot-based localized therapy.

The strategy significantly extends the accessible region, the delivery efficiency, and therapeutic functions of the conventional endoscope and medical robots. As the endoscopy technique and the micro-robotics are still advancing, it is predictable that the integration of these aspects will lead to a promising therapeutic system with highly extended working distance, improved time efficiency for remote delivery and diverse functionalities with high clinical value.

It should be understood that the examples and embodiments described below are for illustrative purposes only and that various modifications or changes in light thereof will be suggested to persons skilled in the art and are to be included within the spirit and purview of this application.

By combining of the dual clinical imaging modalities (for example, an endoscopic view and a US imaging) and magnetic actuation system, the integrated robotic system enables the rapid deployment and high-precision delivery of the microrobots in a real-time manner across the whole-body range towards the hard-to-reach regions, which are inaccessible and even invisible by the conventional endoscope and medical robots. The integration strategy offers a full-clinical imaging technique based therapeutic/intervention system with highly extended working distance, improved time efficiency for targeted delivery and diverse functionalities with high clinical value.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

1. Nelson, B. J., Kaliakatsos, I. K., Abbott, J. J., Microrobots for Minimally Invasive Medicine. *Annu. Rev. Biomed. Eng.* 12, 55-85 (2010).
2. Li, J. X., de Avila. B.-F., Gao, W., Zhang, L. F., Wang. J., Micro/nanorobots for biomedicine: Delivery, surgery, sensing, and detoxification. *Sci. Robot.* 2, eaam6431 (2017).
3. Li, W., Zhang, L., Ge, Y., Xu, X. H., Zhang, B. Y., Qu, W. X., Choi, L. L. Xu, C.-H. Zhang, J. H., Lee, A. F. Weitz. D. A H. Microfluidic fabrication of microparticles for biomedical applications. *Chem. Soc. Rev.* 47, 5646-5683 (2018).
4. Wu, Z. G., Li, L., Yang, Y. R., Hu, P., Li, Y., Yang, S.-Y., Wang, L. V., Gao, W. A microrobotic system guided by photoacoustic computed tomography for targeted navigation in intestines in vivo. *Sci. Robot.* 4, eaax0613 (2019).
5. Wu, Z., Troll, J., Jeong, H., Wei, Q., Stang, M., Ziemssen, F., Wang, Z., Dong, M., Schnichels, S., Qiu, T., Fischer, P. A swarm of slippery micropropellers penetrates the vitreous body of the eye. *Sci. Adv.* 4, eaat4388 (2018).
6. de Avila, B. E., Angsantikul, P., Ramirez-Herrera, D. Soto, E., Teymourian, F., H., Dehaini, D., Chen, Y. J., Zhang, L. F., Wang, J. Hybrid biomembrane-functionalized nanorobots for concurrent removal of pathogenic bacteria and toxins. *Sci. Robot.* 3, eaat0485 (2018).
7. Kim, J. T., Choudhury, U., Jeong, H.-H., Fischer, P. Nanodiamonds That Swim. *Adv. Mater.* 29, 1701024 (2017).
8. Leong, T. G., Randall, C. L., Benson, B. R., Bassik, N., Stern, G. M., Gracias, D. H., Tetherless thermobiochemically actuated microgrippers. *Proc. Natl. Acad. Sci. U.S.A* 106, 703-708 (2009).
9. Gultepe, E., Randhawa, J. S., Kadam, S., Yamanaka, S., Selaru, F. M., Shin, E. J., Kalloo, A. N., Gracias, D. H. Biopsy with Thermally Responsive Untethered Microtools. *Adv. Mater.* 25, 514-519 (2013).
10. Cheng, R., Huang, W. J., Huang, L. J., Yang, B., Mao, L. D., Jin, K. L., ZhuGe, Q. C., Zhao, Y. P. Acceleration of Tissue Plasminogen Activator-Mediated Thrombolysis by Magnetically Powered Nanomotors. *ACS Nano* 8, 7746-7754 (2014).
11. Shao, J. X., Abdelghani, M., Shen, G. Z., Cao, S. P., Williams, D. S., van Hest, J. C. M. Erythrocyte Membrane Modified Janus Polymeric Motors for Thrombus Therapy. *ACS Nano* 12, 4877-4885 (2018).
12. Li, J., Li, X., Luo, T., Wang, R., Liu, C., Chen, S., Li, D., Yue, J., Cheng, S., Sun, D. Development of a magnetic microrobot for carrying and delivering targeted cells. *Sci. Robot.* 3, eaat8829 (2018).
13. Jeon, S., Kim, S., Ha, S., Lee, S., Kim, E., Kim, S. Y., Park, S. H., Jeon, J. H., Kim, S. W., Moon, C., Nelson, B. J., Kim, J., Yu, S.-W., Choi, H. Magnetically actuated microrobots as a platform for stem cell transplantation. *Sci. Robot.* 4, eaav4317 (2019).
14. Medina-Sánchez, M., Schwarz, L., Meyer, A. K., Hebenstreit, F., Schmidt, O. G., Cellular Cargo Delivery: Toward Assisted Fertilization by Sperm-Carrying Micromotors. *Nano Lett.* 16, 555-561 (2015).
15. Ricotti, L., Trimmer, B., Feinberg, A. W., Raman, R., Parker, K. K., Bashir, R., Sitti, M., Martel, S., Dario, P. A. Menciassi, Biohybrid actuators for robotics: A review of devices actuated by living cells. *Sci. Robot.* 2, eaaq0495 (2017).
16. Yu, J. F., Jin, D. D., Chan, K. F., Wang, Q. Q., Yuan, K., Zhang, L. Active Generation and Magnetic Actuation of Microrobotic Swarms in Bio-fluids, *Nat. Commun.* 10, 5631 (2019).
17. Yan, X. H., Zhou, Q., Vincent, M., Deng, Y., Yu, J., Xu, J., Xu, T., Tang, T., L., Bian, Wang, Y., Kostarelos, K., Zhang, L. Multifunctional biohybrid magnetite microrobots for imaging-guided therapy. *Sci. Robot.* 2, eaaq1155 (2017).
18. Yan, X. H., Zhou, Q., Yu, J. F., Xu, T. T., Deng, Y., Tang, T., Feng, Q., Bian, L. M., Zhang, Y., Ferreira, A., Zhang, L. Magnetite Nanostructured Porous Hollow Helical Microswimmers for Targeted Delivery. *Adv. Funct. Mater.* 25, 5333-5342 (2015).
19. Felfoul, O., Mohammadi, M., Taherkhani, S., de Lanauze, D., Xu, Y., Loghin, D., Essa, S., Jancik, S., Houle, D., Lafleur, M., Gaboury, L., Tabrizian, M., Kaou, N., Atkin, M., Vuong, T., Batist, G., Beauchemin, N., Radzioch, D., Martel, S. Magneto-aerotactic bacteria deliver drug-containing nanoliposomes to tumour hypoxic regions. *Nat. Nanotechnol.* 11, 941-947 (2016).
20. Martel, S., Felfoul, O., Mathieu, J. B., Chanu, A., Tamaz, S., Mohammadi, M., Mankiewicz, M., Tabatabaei, N. MRI-based nanorobotic platform for the control of magnetic nanoparticles and flagellated bacteria for target interventions in human capillaries. *Int. J. Rob. Res.* 28, 1169-1182 (2009).
21. Zhang, Y. B., Zhang, L., Yang, L. D., Vong, C. I., Chan, K. F., Wu, W. K. K., Kwong, T. N. Y., Lo, N. W. S., Ip, M., Wong, S. H., Sung, J. J. Y., Chiu, P. W. Y., Zhang, L. Real-time tracking of fluorescent magnetic spore-based microrobots for remote detection of C. diff toxins. *Sci. Adv.* 5, eaau9650 (2019).
22. Zhang, Y. B., Yan, K., Ji, F. T., Zhang, L. Enhanced removal of toxic heavy metals using swarming biohybrid adsorbents, *Adv. Funct. Mater.* 27, 1806340 (2018).
23. Wang, X. P., Qin, X.-H., Hu, C. Z., Terzopoulou, A., Chen, X.-Z., Huang, T.-Y., Maniur-Weber, K., Pane, S., Nelson, B. J. 3D Printed Enzymatically Biodegradable Soft Helical Microswimmers. *Adv. Funct. Mater.* 28, 1804107 (2018).
24. Wang, B., Chan, K. F., Yu, J. F., Wang, Q. Q., Yang, L. D., Chiu, P. W. Y., Zhang, L. Reconfigurable swarms of ferromagnetic colloids for enhanced local hyperthermia. *Adv. Funct. Mater.* 28, 1705802 (2018).
25. Yu, J. F., Wang, B., Du, X. Z., Wang, Q. Q., Zhang, L. Ultra-extensible ribbon-like magnetic microswarm. *Nat. Commun.* 9, 3260 (2018).
26. Palagi, S., Fischer, P. Bioinspired microrobots. *Nat. Rev. Mater.* 3, 113-24 (2018).
27. de Ávila, B. E., Angsantikul, P., Li, J. X., Gao, W., Zhang, L. F., Wang, J., Micromotors Go In Vivo: From Test Tubes to Live Animals. *Adv. Funct. Mater.* 28, 1705640 (2018).
28. Sitti, M., Ceylan, H., Hu, W., Giltinan, J., Turan, M., Yim, S., Diller, E. Biomedical Applications of Untethered Mobile Milli/Microrobots. *Proc. IEEE Inst. Electr. Electron. Eng.* 103, 205-224 (2015).
29. Laschi, C., Mazzolai, B., Cianchetti, M. Soft robotics: Technologies and systems pushing the boundaries of robot abilities. *Sci. Robot.* 1, eaah3690 (2016).
30. Medina Sánchez, M., Magdanz, V., Guix, M., Fomin, V. M., Schmidt, 0. G. Swimming Microrobots: Soft, Reconfigurable, and Smart. *Adv. Funct. Mater.* 28, 1707228 (2018).
31. Huang, H. W., Sakar, M. S., Petruska, A. J., Pane, S., Nelson, B. J., Soft micromachines with programmable motility and morphology. *Nat. Commun.* 7, 12263 (2016).
32. Morimoto, Y., Onoe, H., Takeuchi, S. Biohybrid robot powered by an antagonistic pair of skeletal muscle tissues. Sci. Robot. 3, eaat4440 (2018).
33. Kim, Y., Parada, G. A., Liu, S., Zhao, X. H. Ferromagnetic soft continuum robots. *Sci. Robot,* 4, eaax7329 (2019).
34. Liu, X., Liu, J, Lin S., Zhao, X. H. *Mater. Today* (2020), https://doi.org/10.1016/j.mattod.2019.12.026.
35. Zhao, X. & Kim Y. Soft microbots controlled by nanomagnets. *Nature* 575, 58-59 (2019).
36. Sitti M. Miniature soft robots—road to the clinic. *Nat. Rev. Mater.* 3, 74-75 (2018).
37. Medina-Sanchez, M. S., Schmidt, O. G. Medical microbots need better imaging and control. *Nature* 545, 406-408 (2017).
38. Deng, H., Li, X. L., Peng, Q., Wang, X., Chen, J. P., Li, Y. D. Monodisperse Magnetic Single Crystal Ferrite Microspheres. *Angew. Chem. Int. Ed.* 44, 2785 (2005).
39. Ahmed, D., Baasch, T., Blondel, N., Läubli, N., Dual, J., Nelson, B. J. Neutrophil-inspired propulsion in a combined acoustic and magnetic field. *Nat. Commun.* 8, 770 (2017).
40. Field, R. D., Anandakumaran, P. N., Sia, S. K. Soft medical microrobots: Design components and system integration. *Appl. Phy. Rev.* 6, 041305 (2019).
41. Yu, H., Lu, K., Zhu, J., Wang, J. Stem cell therapy for ischemic heart diseases. *Br. Med. Bull.* 121, 135-154 (2017).
42. Xia, X., Chan, K. F., Wong, G. T. Y., Wang, P., Liu, L., Yeung, B. P. M., Ng, E. K. W., Lau, J. Y. W., Chiu, P. W. Y. Mesenchymal stem cells promote healing of nonsteroidal anti-inflammatory drug-related peptic ulcer through paracrine actions in pigs. *Sci. Transl. Med.* 11, eaat7455 (2019).
43. Okabe, S., Amagase, K. An overview of acetic acid ulcer models—the history and state of the art of peptic ulcer research. *Biol. Pharm. Bull.* 28, 1321-1341 (2005).

The invention claimed is:
1. An integrated robotic system for delivery and on-demand tasks of magnetic devices in a body, comprising:
   a magnetic actuation device;
   a plurality of imaging devices;
   a delivery device; and
   at least one magnetic device;
   wherein the delivery device is configured to deliver the at least one magnetic device to a targeted location of the body,
   wherein the at least one magnetic device comprises a soft magnetic microrobot configured to react to surroundings by self-alternating a shape or structure of the soft magnetic microrobot, and
   wherein the soft magnetic microrobot is formed by cells and magnetic particles without a rigid scaffold, and wherein the cells include a stem cell spheroid doped with a magnetic particle intracellularly.
2. The integrated robotic system of claim 1, wherein the magnetic actuation device comprises a permanent magnet or an electromagnetic coil system.
3. The integrated robotic system of claim 1, wherein the plurality of imaging devices comprise two or more selected from an endoscopy device, a ultrasound imaging device, a fluoroscopy device, a magnetic resonance imaging device, a positron emission tomography device, a X-ray computed tomography device, a photoacoustic imaging device, a fluorescence imaging device, a digital camera, and magnetic field sensors, configured to capture images of the at least one magnetic device and tracking locations of the at least one magnetic device in the body.
4. The integrated robotic system of claim 1, wherein the delivery device is an endoscope, a catheter, a guidewire, or a tube.
5. The integrated robotic system of claim 1, wherein the body is of a human and the targeted location comprises one or more selected from a gastrointestinal tract, a brain, an ear, a nose, a throat, an eye, a blood vessel, a heart, a respiratory tract, a liver, a pancreas, a hepatopancreatic duct, a urinary tract, and a reproductive tract.
6. The integrated robotic system of claim 1, wherein clinical applications are diagnostic and/or therapeutic applications comprising one or more selected from a targeted delivery of microrobots, drugs, or cells, retrieval of microrobots, drugs, or cells, sensing, tissue manipulation, tissue removal, and tissue retraction.
7. The integrated robotic system of claim 1, wherein upon being compressed, the soft magnetic microrobot recovers to an original shape and structure after the compression is retracted.
8. The integrated robotic system of claim 1, wherein when the soft magnetic microrobot passes through a narrow channel with an inner width smaller than an original diameter of the soft magnetic microrobot, the shape or structure of the soft magnetic microrobot is compressed in a reconfigurable manner and then the soft magnetic microrobot recovers the shape or structure.
9. A method for controlling an integrated robotic system according to claim 1, the method comprising:
   forming the at least one magnetic device through a co-culture process of cells and magnetic particles, the cells being doped with the magnetic particles intracellularly; and
   delivering the at least one magnetic device in two steps, wherein the two steps comprises a long-range delivery step configured to move the at least one magnetic device to travel a long distance to a region in proximity of the targeted location in the body and a precise magnetic actuation delivery step configured to move the at least one magnetic device with high precision to the targeted location in the body after the long-range delivery step.

10. The method of claim 9, wherein the long-range delivery step includes controlling the delivery device to move the at least one magnetic device to travel a distance to a region in proximity of the targeted location in the body.

11. The method of claim 9, wherein the precise magnetic actuation delivery step includes controlling the magnetic actuation device to move the at least one magnetic device with millimeter-precision to the targeted location in the body after the long-range delivery step.

12. The method of claim 9, wherein during the long-range delivery step, a first imaging device of the plurality of imaging devices captures images of the at least one magnetic device and tracks locations of the at least one magnetic device in the body.

13. The method of claim 12, wherein during the precise magnetic actuation delivery step, a second imaging device of the imaging devices that is different from the first imaging device captures images of the at least one magnetic device and tracks locations of the at least one magnetic device in the body.

* * * * *